United States Patent

Yoneda et al.

[11] Patent Number: 6,066,762
[45] Date of Patent: May 23, 2000

[54] PROCESS FOR THE PRODUCTION OF CARBONYL COMPOUND

[75] Inventors: Noriyuki Yoneda, Tokyo; Takeshi Minami, Yokohama; Yoshihiro Nakagawa, Kagoshima-ken; Ikuo Ohta, Yokohama; Akihisa Yamaguchi, Yokohama; Hideki Sugiyama, Yokohama; Fumihiko Uemura, Yokosuka, all of Japan

[73] Assignee: Chiyoda Corporation, Yokohama, Japan

[21] Appl. No.: 08/997,552

[22] Filed: Dec. 23, 1997

[30] Foreign Application Priority Data

| Dec. 30, 1996 | [JP] | Japan | 8-358624 |
| Feb. 19, 1997 | [JP] | Japan | 9-051069 |
| Mar. 5, 1997 | [JP] | Japan | 9-067343 |
| Mar. 5, 1997 | [JP] | Japan | 9-067344 |

[51] Int. Cl.$^7$ .................................................. C07C 51/12
[52] U.S. Cl. ........................... 562/519; 562/517; 562/607
[58] Field of Search ..................... 562/519, 517, 562/607

[56] References Cited

U.S. PATENT DOCUMENTS

| 3,717,670 | 2/1973 | Schultz | 562/519 |
| 5,334,755 | 8/1994 | Yoneda et al. | 562/519 |
| 5,364,963 | 11/1994 | Minami et al. | 562/519 |
| 5,380,929 | 1/1995 | Erpenbach et al. | 562/519 |
| 5,416,237 | 5/1995 | Aubigne et al. | 562/519 |
| 5,420,345 | 5/1995 | Smith | 562/519 |
| 5,442,107 | 8/1995 | Beevor et al. | 562/519 |

FOREIGN PATENT DOCUMENTS

| 161874 | 11/1985 | European Pat. Off. . |
| 265140 | 4/1988 | European Pat. Off. . |

*Primary Examiner*—Paul J. Killos
*Assistant Examiner*—Taylor V Oh
*Attorney, Agent, or Firm*—Armstrong, Westerman, Hattori, McLeland & Naughton

[57] ABSTRACT

A process for the production of a carbonyl compound such as acetic acid by reacting a carbonylatable compound such as methanol with a carbon monoxide in the presence of a carbonylation catalyst containing a noble metal complex supported on a porous, cross-linked vinylpyridine resin at a temperature of 140–250° C., a carbon monoxide partial pressure of 7–30 kg/cm$^2$ and a hydrogen partial pressure of 0.1–5 kg/cm$^2$ to obtain a liquid product containing the carbonyl compound and an unreacted CO-containing gas product. The water content and the carbonylation degree of the liquid product within the reactor are maintained at 0.5–10% by weight and 0.5–0.9, respectively, The carbonyl compound is separated from the liquid product in a flasher and/or a distillation tower formed of titanium or a titanium-palladium alloy. The liquid product is introduced into a pressure reducing valve and then mixed with the CO-containing gas product before being fed to the flasher and/or distillation tower.

24 Claims, 11 Drawing Sheets

PROCESS FOR THE PRODUCTION OF CARBONYL COMPOUND

BACKGROUND OF THE INVENTION

This invention relates to a process for the production of a carbonyl compound by reaction of a carbonylatable compound such as an alcohol, a carboxylic acid ester, an ether or an olefin with carbon monoxide in the presence of a carbonylation catalyst containing a noble metal complex supported on a porous, crosslinked resin having pyridine nuclei.

It is known to produce a carbonyl compound by reaction of a carbonylatable compound such as an alcohol, a carboxylic acid ester, an ether or an olefin with carbon monoxide (CO) in the presence of a carbonylation catalyst containing a noble metal complex supported on a porous, crosslinked resin having pyridine nuclei. Examples of known processes of this class include the production of acetic acid by carbonylation of methanol, the production of acetic anhydride by carbonylation of methyl acetate and production of an aldehyde by hydroformylation of an olefin.

For example, U.S. Pat. No. 5,155,261 discloses a process for producing acetic acid by reacting methanol in a solvent with CO in the presence of an alkyl iodide and a solid catalyst containing rhodium complex supported on a porous, crosslinked vinyl pyridine resin (hereinafter referred to as VP resin). In such a process, there are obtained a liquid product containing acetic acid, unreacted methanol, methyl iodide, a solvent and by-products such as methyl acetate, propionic acid, water and hydrogen iodide, and a gaseous product containing an reacted CO, methyl iodide and by-products such as $CO_2$, $H_2$ and $CH_4$.

The above process when applied to an industrially acceptable continuous mode generally includes a reaction step in which the carbonylatable compound is reacted with CO in the presence of the supported catalyst to produce a carbonyl compound, a separation step in which the liquid product is separated into the carbonyl compound and a residual liquid, and a recycling step in which the residual liquid is recycled into the reaction step. Such a process has been found to encounter the following problems.

First, a small amount of the noble metal is apt to be liberated from the solid catalyst and is transferred into the liquid product, so that the catalyst activity of the solid catalyst is reduced. Further, the liberated noble metal when introduced together with the liquid product into the separation step is apt to deposit onto the inside wall of the separation device such as a distillation tower and can no longer be recovered. The liberation of the noble metal from the solid catalyst also occurs when the porous VP resin is broken during the reaction step.

Another problem is that the reactor, the separator, etc. are apt be corroded because of the high corrosiveness of the liquid product. Thus, it is necessary to use a highly stable metal material such as zirconium or Hastelloy B. This causes increased apparatus costs.

A further problem is that by-products such as acetaldehyde and its derivatives including crotonaldehyde, 2-ethylcrotonaldehyde, ethanol, propionic acid, ethyl iodide, butyl iodide and hexyl iodide are produced so that the permanganate time of the carbonyl product is adversely affected and the iodine content thereof is increased.

SUMMARY OF THE INVENTION

It is, therefore, an object of the present invention to provide a process for the production of a carbonyl compound by reaction of a carbonylatable compound with CO in the presence of a catalyst having a noble metal complex supported on a VP resin, which process has solved the above problems.

Another object of the present invention is to provide a process of the above-mentioned type in which the loss of the noble metal can be prevented.

It is a further object of the present invention to provide a process of the above-mentioned type in which the the breakage of the VP resin and liberation of the noble metal can be minimized.

It is yet a further object of the present invention to provide a process of the above-mentioned type in which liquid product obtained by the reaction can show reduced metal corrosiveness.

In accomplishing the foregoing objects, there is provided in accordance with one aspect of the present invention a process for the production of a carbonyl compound, comprising the steps of:

(a) reacting a carbonylatable compound with a carbon monoxide feed in a reactor in the presence of a carbonylation catalyst including a noble metal complex supported on a porous, cross-linked vinylpyridine resin to obtain a liquid product containing the carbonyl compound; and (b) discharging said liquid product from said reactor and separating said carbonyl compound from said discharged liquid product in a flasher and/or a distillation tower, wherein step (a) is performed at a temperature of 140–250° C., a carbon monoxide partial pressure of 7–30 $kg/cm^2$ and a hydrogen partial pressure of 0.1–5 $kg/cm^2$ while maintaining the water content and the carbonylation degree of the reaction solution within the reactor at 0.5–10% by weight and within the range of 0.5–0.9, respectively, and wherein the water content and the carbonylation degree of said discharged liquid product are maintained at not greater than 10% by weight and not greater than 0.9, respectively.

In another aspect, the present invention provides a process for the production of a carbonyl compound, comprising the steps of:

(a) reacting a carbonylatable compound with a carbon monoxide feed in a reactor in the presence of a carbonylation catalyst including a noble metal complex supported on a porous, cross-linked vinylpyridine resin to obtain a liquid product containing the carbonyl compound; and (b) discharging said liquid product from said reactor and introducing said discharged liquid product into a first or a series of first to n-th distillation towers successively, where n is at least two, thereby to separate said carbonyl compound from said liquid product, wherein step (a) is performed at a temperature of 140–250° C., a carbon monoxide partial pressure of 7–30 $kg/cm^2$ and a hydrogen partial pressure of 0.1–5 $kg/cm^2$ while maintaining the water content and the carbonylation degree of the reaction solution within said reactor at 0.5–10% by weight and within the range of 0.5–0.9, respectively, wherein the water content and the carbonylation degree of said discharged liquid product are maintained at not greater than 10% by weight and not greater than 0.9, respectively, and wherein the water content of the fraction containing said carbonyl compound obtained in said first distillation tower is adjusted at 3,000 ppm by weight or less.

The present invention also provides a process for the production of a carbonyl compound, comprising the steps of:

(a) reacting a carbonylatable compound with carbon monoxide in a reactor in the presence of a carbonylation catalyst including a noble metal complex supported on a porous, cross-linked vinylpyridine resin to obtain a liquid product containing the carbonyl compound; and (b) separating said carbonyl compound from said liquid product in a flasher and/or a distillation tower, wherein step (a) is performed while maintaining the water content of said liquid product at not greater than 10% by weight, and wherein the interior surface of said flasher and/or distillation tower is formed of titanium or a titanium-palladium alloy.

The present invention further provides a process for the production of a carbonyl compound, comprising the steps of:

(a) reacting a carbonylatable compound with carbon monoxide in a reaction zone in the presence of a carbonylation catalyst including a noble metal complex supported on a porous, cross-linked vinylpyridine resin to obtain a liquid product containing the carbonyl compound and a gas product containing unreacted carbon monoxide;

(b) discharging said liquid product from said reaction zone and introducing same into a pressure reducing device to reduce the pressure of said discharged liquid product to obtain a pressure-reduced liquid product;

(c) withdrawing said gas product from said reaction zone;

(d) mixing said pressure-reduced liquid product with said gas product to form a mixture; and (e) separating said carbonyl compound from said mixture in a separation zone.

The present invention further provides a process for the production of a carbonyl compound, comprising the steps of:

(a) reacting a carbonylatable compound with carbon monoxide in the presence of a carbonylation catalyst including a noble metal complex supported on a porous, cross-linked vinylpyridine resin to obtain a liquid product containing the carbonyl compound; and (b) separating said carbonyl compound from said liquid product, step (a) being performed while maintaining the concentration of pyridine compounds in said liquid product within the range of 0.5–200 ppm by weight in terms of elemental nitrogen.

BRIEF DESCRIPTION OF THE DRAWINGS

Other objects, features and advantages of the present invention will become apparent from the detailed description of the preferred embodiments which follows, when considered in light of the accompanying drawings, in which.

DETAILED DESCRIPTION OF THE PREFERRED EMBODIMENTS OF THE INVENTION

Figure 1:
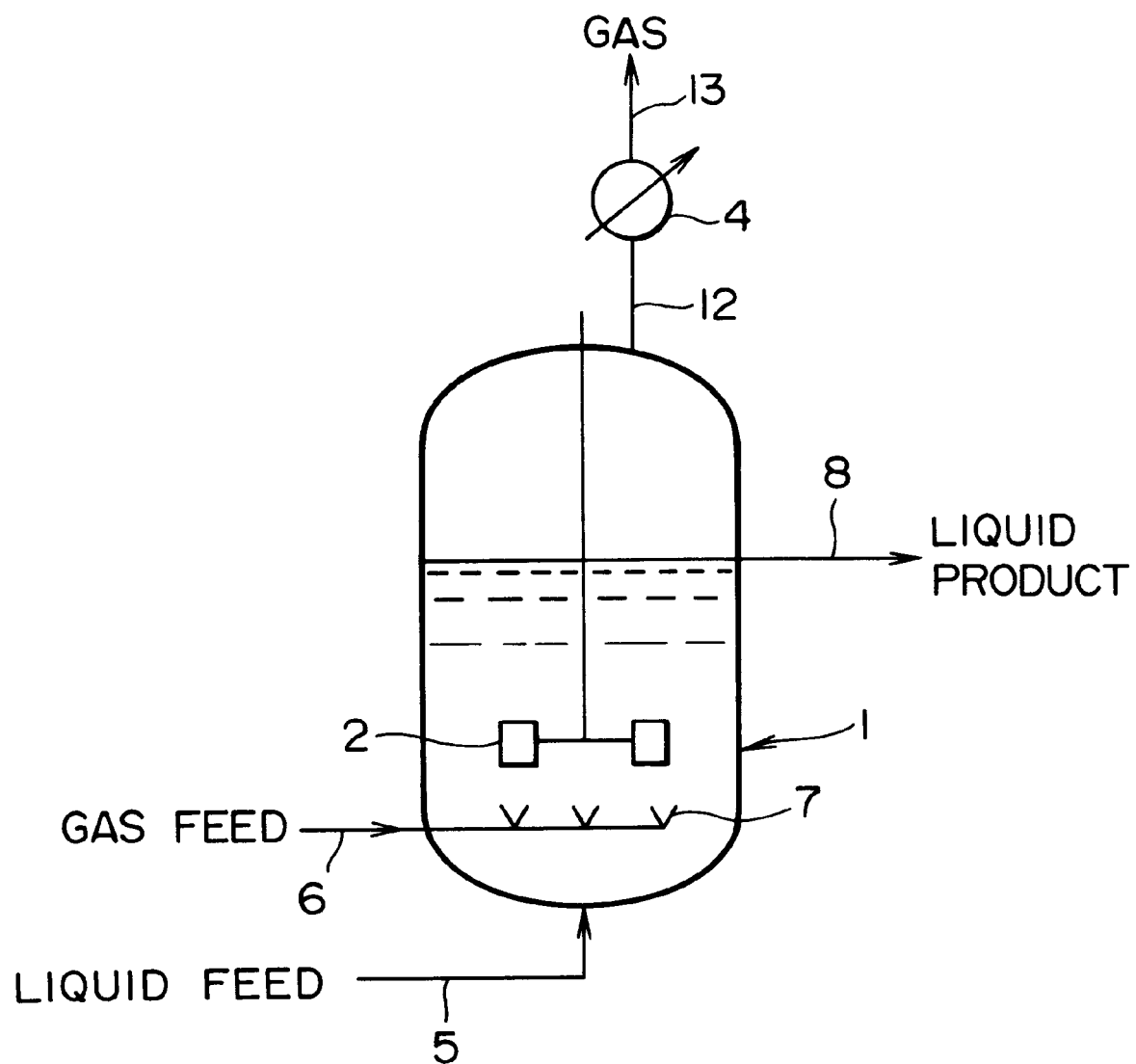
FIGS. 1–3 are each an elevational view diagrammatically showing a reactor useful for carrying out the catalytic carbonylation reaction of the process according to the present invention.

The process according to the present invention includes a reaction step in which a carbonylatable compound is reacted with CO in the presence of a porous, crosslinked vinyl pyridine resin (VP resin) on which a noble metal complex is supported to produce a carbonyl compound.

The noble metal complex may be, for example, a rhodium complex, a cobalt complex, a ruthenium complex or an iridium complex. For the production of acetic acid as the carbonyl compound, the use of rhodium is preferred. The carbonylatable compound may be, for example, an alcohol, a carboxylic acid ester, an ether or an olefin. Illustrative of suitable carbonylatable alcohols are benzyl alcohol, furfuryl alcohol and aliphatic alcohols having 1–6 carbon atoms, such as methanol, ethanol, propanol and butanol. Illustrative of suitable carbonylatable ethers are aliphatic ethers having 2–12 carbon atoms such as dimethyl ether, diethyl ether, dipropyl ether and methyl ethyl ether. Illustrative of suitable esters are those of aliphatic carboxylic acids having 1–6 carbon atoms with aliphatic alcohols having 1–6 carbon atoms, such as methyl acetate, ethyl acetate, propyl acetate, butyl acetate, amyl acetate, hexyl acetate, methyl propionate, ethyl propionate, propyl propionate, butyl propionate, hexyl propionate, methyl butyrate, ethyl butyrate, propyl butyrate, butyl butyrate, amyl butyrate, hexyl butyrate, methyl valerate, ethyl valerate, propyl valerate, methyl caproate, ethyl caproate and propyl caproate.

An alcohol, an ether and an ester are carbonylated as follows ($R^1$ and $R^2$ each represent a hydrocarbyl group):

(1) Alcohol carbonylation:

$R^1OH+CO \rightarrow R^1COOH$ (2) Ether carbonylation:

$R^1OR^2+H_2O \rightarrow R^1OH+R^2OH$ $R^1OH+CO \rightarrow R^1COOH$ $R^2OH+CO \rightarrow R^2COOH$ (3) Ester carbonylation:

$R^1COOR^2+H_2O \rightarrow R^1COOH+R^2OH$

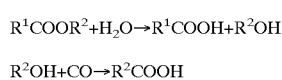

$R^2OH+CO \rightarrow R^2COOH$

The VP resin may be produced by copolymerizing a vinylpyridine monomer with an aromatic compound having two vinyl groups as a crosslinking agent. The copolymerization method is well known in the art and may be, for example, a method in which a precipitant is added, a method in which a linear polymer is added, a method in which a swelling agent and a precipitant are added, and a method in which a diluent and a linear polymer are added. The method disclosed in Japanese Published Examined Patent Application No. 61-25731 may be particularly suitably used. In this method, a mixture containing a vinyl pyridine monomer, a cross-linking agent having two vinyl groups and, optionally, a vinyl monomer is reacted in the presence of a radical polymerization catalyst, a suspension stabilizing agent and a precipitant using an aqueous suspension polymerization technique. The stabilizer may be a water-soluble polymer such as polyvinyl alcohol, hydroxyethyl cellulose, carboxymethyl cellulose, sodium polymethacrylate, sodium polyacrylate, starch, gelatin, or an ammonium salt of styrene/meleic anhydride copolymer, or an inorganic salt such as calcium carbonate, calcium sulfate, bentonite or magnesium silicate. The precipitant is an organic liquid which serves to function as a good solvent for the monomer but as a poor solvent for the copolymer produced. Examples of the precipitant includes hydrocarbons having 5–10 carbon atoms such as isooctane, alcohols and esters. The polymerization degree of the VP resin may be controlled by control of the amount of the crosslinking agent. The pore volume and the average pore diameter may be controlled by selection of the kind and amount of the precipitant. Suitable selection of the kind and amount of the suspension stabilizer and the reaction temperature is also effective to control the pore characteristics of the VP resin.

Illustrative of suitable vinylpyridine monomers for the production of the VP resin are 4-vinylpyridine, 2-vinylpyridine and 2- and 4-vinylpyridine derivatives having a lower alkyl group such as a methyl group or ethyl group on the pyridine ring. The vinylpyridine monomer may be used in conjunction with an aromatic vinyl monomer such as styrene or vinyltoluene. Such a vinyl monomer is used in an amount of 30 mole % or less, preferably 1–30 mole %, more preferably 5–20 mole % based on the total mole of total monomers. Illustrative of suitable cross-linking agents are aromatic divinyl compounds such as divinylbenzene and divinyltoluene and aliphatic divinyl compounds such as ethylene glycol diacrylate and butadiene. Commercially available divinylbenzene usually contains about 50 mole % of ethylvinylbenzene. Such divinylbenzene may be used as such for the purpose of the present invention. The amount of the crosslinking agent is determined according to the intended crosslinking degree.

It is preferred that the vinylpyridine resin have a crosslinking degree of 10–70%, preferably 30–60%, a surface area of 5–80 $m^2/g$, preferably 10–40 $m^2/g$, a pore volume of 0.15–0.5 cc/g, preferably 0.2–0.4 cc/g, and an average pore diameter of 20–100 nm, preferably 30–90 nm for reasons of an improved catalyst life, good mechanical strengths (e.g. resistance to abrasion and crushing) and high catalytic activity.

The term "crosslinking degree" herein is defined as follows:

Crosslinking degree (%)=(A/B)×100 wherein A represents the weight of the crosslinking agent contained in the VP resin and B represents the weight of the vinylpyridine monomer units of the VP resin.

The "pore volume" of the VP resin is measured by the mercury penetration method using Mercury Pressure Porosimeter Model 70 (manufactured by Carlo Elba Inc., Italy) with a mercury surface tension of 474 dyne/cm at 25° C., a contact angle of 140 degrees and an absolute mercury pressure varying from 1 to 200 $kg/cm^2$.

The term "average pore diameter" used herein is defined as follows:

Average pore volume (nm)=4(C/D)×$10^3$ wherein C represents the pore volume (cc/g) of the VP resin and D represents the surface area ($m^2/g$) of the VP resin measured by the B. E. T. method.

The VP resin is generally used in the form of beads, preferably spheres, having a particle size of 0.01–4 mm, preferably 0.1–2 mm, more preferably 0.4–2 mm.

The VP resin is loaded with a noble metal complex in any suitable manner. The amount of the noble metal complex loaded on the VP resin is 0.2–5% by weight, preferably 0.5–3.0% by weight, in terms of elemental metal, based on the weight of the VP resin.

One example of suitable noble metal catalyst is rhodium complex loaded VP resin in which rhodium complex ion $[Rh(CO)_2I_2]^-$ is bonded to at least part of the pyridine nuclei of the VP resin as follows:

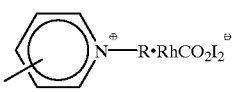

where R represents a hydrogen atom or a lower alkyl group.

The loading of the VP resin with the rhodium complex may be performed by a method which includes the steps of (a) contacting the VP resin with an aqueous solution containing rhodium ion so that the rhodium ion is bound to the resin, and (b) contacting the rhodium ion-carrying VP resin with carbon monoxide and an alkyl iodide (RI) in an organic solvent so that the rhodium ion is converted to a rhodium complex bound to the resin, as follows:

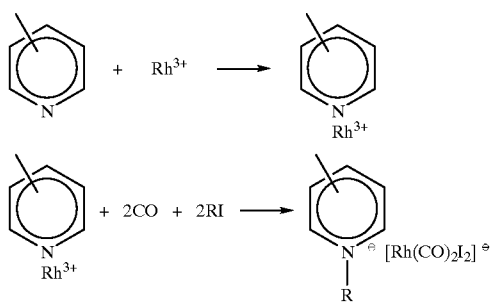

The loading of the VP resin with the rhodium complex may be also performed by contacting the VP resin with a rhodium salt in a solvent containing an alkyl iodide under a pressure of carbon monoxide. This method may be carried out by contacting the rhodium salt with the VP resin under the conditions generally adopted in the catalytic carbonylation of methanol. During the course of the above reaction, the pyridine ring of the VP resin are quaternized with the alkyl iodide to form a pyridinium salt to which is ionically bonded a rhodium carbonyl complex $[Rh(CO)_2I_2]^-$ formed by reaction of the rhodium salt, alkyl iodide and carbon monoxide.

Examples of the rhodium salts include rhodium halides such as rhodium chloride, rhodium bromide and rhodium iodide and rhodium carboxylate such as rhodium acetate and rhodium propionate. Illustrative of suitable alkyl iodides are lower alkyl iodides having 1–5 carbon atoms, such as methyl iodide, ethyl iodide and propyl iodide. The use of methyl iodide is preferred. The alkyl iodide is used in an amount of 2–2,000 moles, preferably 50–500 moles, per mole of the rhodium salt. The carbon monoxide pressure under which the rhodium salt is contacted with the VP resin in the presence of the alkyl iodide is 7–30 $kg/cm^2G$, preferably 10–20 $kg/cm^2G$.

In the production of acetic acid which is one of the preferred embodiments according to the present invention, the carbonylatable compound selected from methanol and dimethyl ether is reacted with CO in an organic solvent in the presence of an alkyl iodide and a catalyst having a rhodium complex supported on the VP resin. The reaction may be performed using any desired reactor such as of a packed bed-type reactor, a stirred tank-type reactor or an expansion-type reactor.

The amount of the catalyst charged in the reactor is generally 2–40% by weight based on the weight of the reaction solution contained in the reactor. In the case of a stirred tank-type reactor, the catalyst is preferably charged in the reactor in an amount of 2–25% by weight based on the weight of the reaction solution within the reactor.

Any organic solvent may be used for the purpose of the present invention. A carbonyl group-containing compound having at least two carbon atoms is suitably used. Such a compound may be, for example, a saturated aliphatic acid such as acetic acid, propionic acid or butyric acid, an ester such as methyl acetate or ethyl acetate, an aromatic acid such as benzoic acid, or a mixture thereof. The use of acetic acid is especially preferred. The organic solvent preferably contains water in an amount of 0.05–50% by weight, more preferably 0.1–20% by weight, most preferably 0.5–10% by weight, based on the weight of the reaction solution within the reactor. The alkyl iodide is preferably a lower alkyl iodide having 1–6 carbon atoms, such as methyl iodide.

It is preferred that the content of the organic solvent in the reactor be at least 0.3 part by weight, more preferably at least 2.4 parts by weight per part by weight of the carbonylatable compound present in the reaction solution within the reactor. By using the organic solvent in such a specific amount, the catalyst can exhibit high catalytic activity and the dissociation of rhodium species from the polymer substrate can be minimized, so that the reaction can be efficiently performed in a stable manner. Additionally, the use of the organic solvent in the specific amount can reduce the carbon monoxide partial pressure to, for example, 7 kg/cm$^2$. This is advantageous from the standpoint of economy because it is not necessary to use a highly pressure-resisting reactor. The term "the reaction solution within the reactor" used herein is variable according to the type of the reactor used. Since the carbonylatable compound is consumed as the reaction proceeds, the relative amount of the organic solvent increases as the reaction proceeds. Thus, in the case of a batch type reactor, for example, the reaction solution within the reactor may be the raw material feed introduced into the reactor. In the case of a continuous flow, stirred tank-type reactor, the reaction solution within the reactor may be the liquid product continuously discharged from the reactor. In the case of a piston flow type reactor, the solution may be the whole feed, inclusive of recycled solutions, to the reactor.

The carbonylation is generally performed at a temperature of 140–250° C., preferably 160–230° C. and a carbon monoxide partial pressure of at least 7 kg/cm$^2$, preferably 7–30 kg/cm$^2$, more preferably 10–20 kg/cm$^2$. The total pressure in the reactor is preferably 15–60 kg/cm$^2$G, more preferably 15–30 kg/cm$^2$G. In the case of the production of acetic anhydride, the carbon monoxide partial pressure is preferably 7–60 kg/cm$^2$. The alkyl iodide is used in an amount effective to promote the methanol carbonylation, generally in an amount of 1–40% by weight, preferably 5–30% by weight, based on the weight of the solution contained in the reactor. The rhodium loaded catalyst is used in a catalytically effective amount, generally in an amount of at least 50 ppm by weight, preferably at least 300 ppm by weight, more preferably at least 600 ppm by weight, in terms of elemental rhodium, based on the weight of the solution contained in the reactor.

The methanol carbonylation using methyl iodide as a co-catalyst involves the following side reactions (2) and (3) in addition to the main reaction (1):

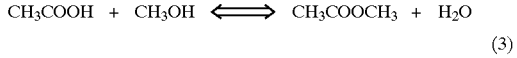

$$CH_3OH + CO \Longrightarrow CH_3COOH \quad (1)$$

$$CH_3COOH + CH_3OH \Longleftrightarrow CH_3COOCH_3 + H_2O \quad (2)$$

$$2CH_3OH \Longleftrightarrow CH_3OCH_3 + H_2O \quad (3)$$

In order to obtain acetic acid with a high yield, it is necessary that the reaction (1) be allowed to selectively proceed while inhibiting the side reactions (2) and (3). To this end, it is effective to use methyl acetate as the solvent or a water-containing organic solvent. In this case, methyl acetate is preferably mixed with the carbonylatable compound (methanol) prior to the introduction into the reactor. The amount of methyl acetate is preferably at least 1.5 parts by weight, more preferably at least 3 parts by weight, per part by weight of the carbonylatable compound. The water-containing solvent is preferably mixed with the carbonylatable compound prior to the introduction into the reactor. The amount of water is preferably at least 0.3 part by weight, more preferably at least 0.5 part by weight, per part by weight of the carbonylatable compound.

The reactor used for carrying out the above reaction will be next described. Referring to FIG. 1, designated generally as 1 is a reactor of a stirred tank-type in which a mechanical stirrer 2 is disposed. In performing the carbonylation, catalyst particles are placed in the reactor 1 and a mixed liquid containing a solvent, a raw material carbonylatable compound and an alkyl iodide is continuously fed through a line 5 into the reactor 1. The stirrer 2 is started to rotate and a carbon monoxide gas is injected into the mixture through a line 6 and nozzles 7. A part of the reaction solution is discharged through a line 8 and a gas phase containing unreacted carbon monoxide, by-product gases (H$_2$ and CO$_2$) and vapors of the solution is withdrawn overhead from the reactor 1 through a line 12 and is cooled in a condenser 4. Condensable components in the gas phase is returned to the reactor 1, while the non-condensed gas is discharged through a line 13.

Figure 2:
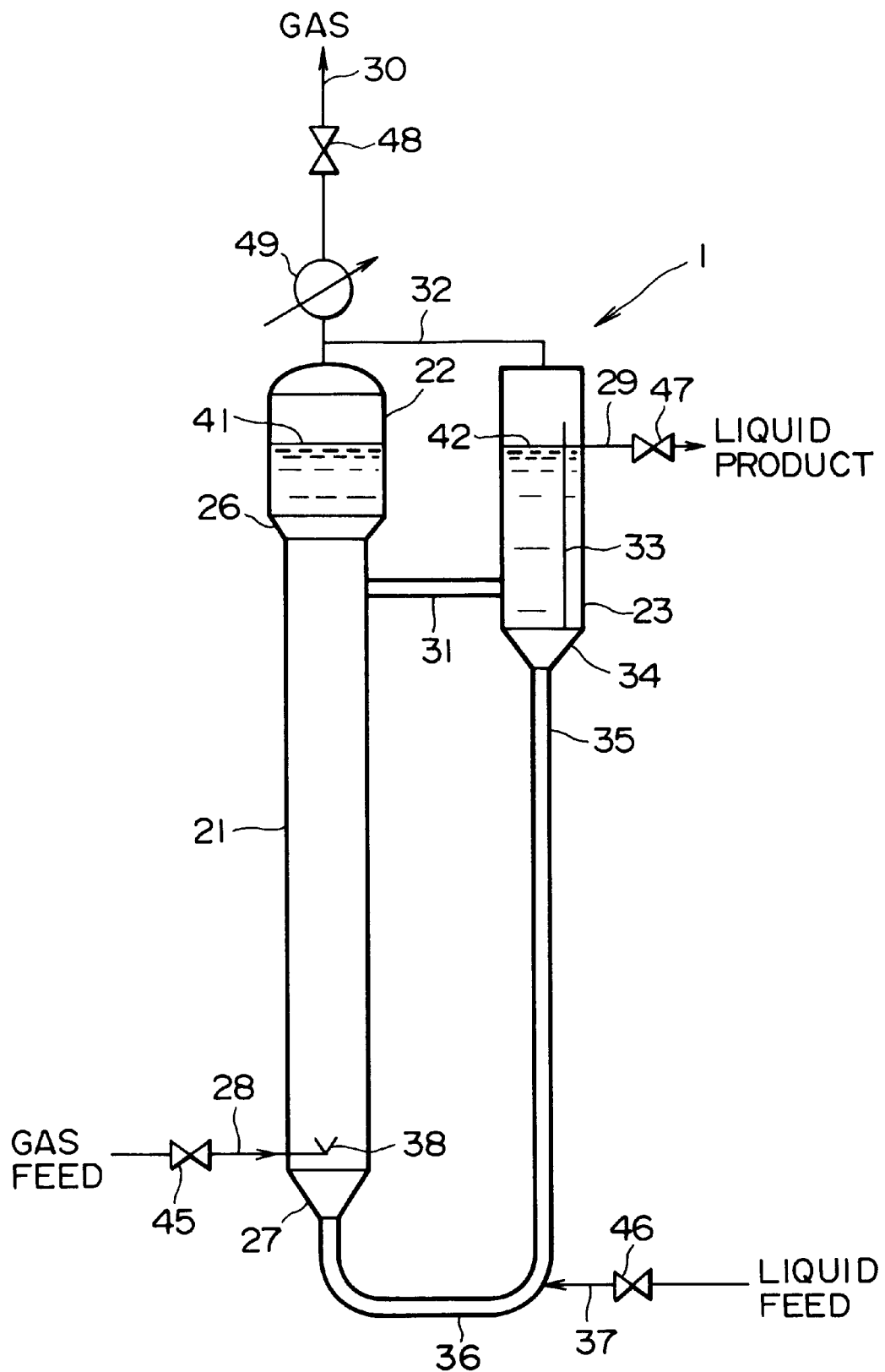

FIG. 2 depicts another embodiment of the carbonylation reactor 1. The reactor 1 includes a vertically extending cylindrical vessel 21 adapted for containing the liquid and the catalyst particles. The height of the vessel 21 is preferably 5–100 times, more preferably 10–20 times, that of the inside diameter thereof. A liquid feed conduit 37 is connected to a lower portion of the vessel 21 for feeding the liquid to the vessel 21 therethrough. Also connected to the lower portion of the vessel 21 is a gas feeding conduit 28 for feeding the gas into the vessel 21 therethrough. A gas injection nozzle 38 is connected to the conduit 28 so that the gas is injected from the nozzle 38 and is bubbled through the liquid contained in the vessel 21. As a consequence of the gas injection, there is formed an upwardly flowing mixture including the liquid, the particles and the gas within the vessel 21. The nozzle 38 may have only one gas injection hole but preferably has a plurality of gas injection holes for forming fine gas bubbles. The force by which the catalyst particles are upwardly moved through the vessel 21 depends upon the linear velocity of the liquid upwardly flowing therethrough. Thus, by controlling the linear velocity of the liquid in the vessel 21 at a level higher than that at which the catalyst particles fall by gravity in the liquid, it is possible to upwardly move the catalyst particles through the vessel 21. The linear velocity of the liquid may be controlled by the rate of the gas feed through the conduit 28.

Designated as 22 is a first separating chamber connected to an upper end of the vessel 21 through an upwardly enlarged section 26 for receiving the upwardly flowing mixture from the vessel 21. The chamber 22 has a horizontal sectional area which is 1–10 times, preferably 2–5 times, as large as that of the vessel 21. In the chamber 22, the mixture is separated by gravity into a first gas phase, a supernatant liquid phase and a phase rich in the catalyst particles. Since the horizontal sectional area of the chamber 22 is larger than that of the vessel 21, the linear velocity of the liquid is reduced upon entering the chamber 22 so that the catalyst particles contained therein precipitate to form the catalyst particles-rich phase in a region including the bottom of the chamber 22 and an upper portion of the vessel 21.

A gas discharge conduit 30 is connected to a top portion of the separating chamber 22 for withdrawing the first gas phase above the liquid level 41.

Designated as 23 is a second separating chamber. The second separating chamber 23 is vertically extended with the inside diameter being preferably 0.5–5 times, more preferably 1–3 times, that of the vessel 21. The second chamber 23 is connected to an upper portion of the vessel 21 through a connecting pipe 31, so that a portion the catalyst particles-rich phase which has been separated in the first separating chamber 22 is introduced, together with a portion of the mixture upwardly flowing through the vessel 21, into the second chamber 23 through the pipe 31 and is separated into a second gas phase and a catalyst particle-containing liquid. The connecting pipe 31 is generally oriented horizontally or downwarly toward the second chamber 23. A supernatant liquid phase discharging conduit 29 is connected to the second separating chamber 23. Designated as 33 is a flow control plate suitably disposed to prevent the gas from discharging through the conduit 29 together with the supernatant liquid phase.

A gas withdrawing conduit 32 extends from a top portion of the second chamber 23 and is joined to the gas discharge conduit 30, so that the second gas phase above the liquid level 42 in the second chamber 23 is discharged from the second chamber 23 and withdrawn together with the first gas phase from the separating chamber 22.

A recycling path including pipes 35 and 36 extends between the second chamber 23 and a lower portion of the vessel 21 for recycling the catalyst particle-containing liquid from the second chamber 23 to the vessel 22 by gravity. Because the gas separation is carried out in both first and second chambers 22 and 23, the content of the gas in the catalyst particle-containing liquid formed in the second chamber 23 is very small, so that the difference in specific gravity between the mass in the vessel 21 and the mass in the recycling path 35 and 36 is significantly great. Therefore, the embodiment shown in FIG. 2 provides efficient recycling and effective contact of the catalyst particles with the gas and liquid.

Designated as 45–48 are flow control valves and as 49 is a condenser. Condensed components in the gas phase is returned to the chamber 22.

Figure 3:
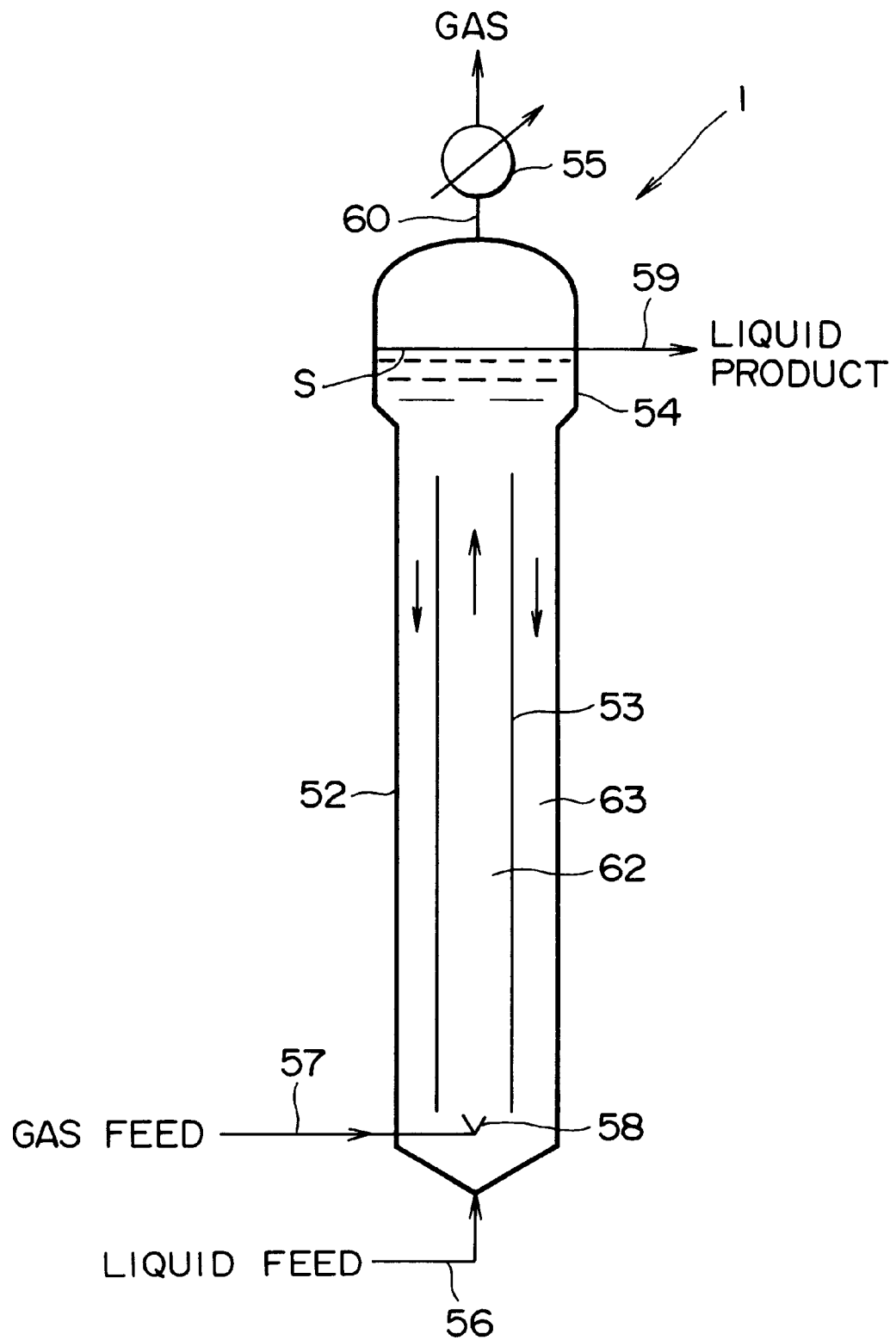

FIG. 3 depicts a further embodiment of a carbonylation reactor 1. The reactor 1 includes an outer vertically extending cylindrical housing 52 and an inner vertically extending cylindrical pipe 53 which defines a contacting zone 62 therein and which is coaxially placed inside the housing 52 to define an annular recycling path 63 therebetween. Similar to the foregoing embodiments, a liquid feed conduit 56 and a gas feeding conduit 57 are connected to a lower portion of the housing 52. A gas injection nozzle 58 is connected to the conduit 57. Disposed above the housing 52 is a separating chamber 54 having a horizontal sectional area greater than that of the housing 52. A gas discharge conduit 60 having a condenser 55 is connected to a top portion of the separating chamber 54 and a liquid discharge conduit 59 is connected to an upper portion of the separating chamber 54.

The operation of the above reactor 1 is as follows. After placing the catalyst particles in the housing 52, the liquid is fed from the conduit 56 to fill the housing 52 up to a predetermined level. The gas is then injected from the nozzle 58 so that the liquid level is raised to the position "S". The feed of the gas is continued while feeding the liquid from the conduit 56. Thus, there is formed an upwardly flowing stream of a mixture of the gas, liquid and catalyst particles in the contacting zone 62. The mixture is separated into a gas phase which is withdrawn overhead through the line 60, a supernatant liquid phase which is discharged through the line 59 and a catalyst particles-rich phase which is recycled through the recycling path 63 to the bottom of the contacting zone 62.

The carbonylation process according to the present invention will now be described with reference to FIG. 4. For simplicity of explanation, the following description will be made on the production of acetic acid by reaction of methanol with CO in the presence of methyl iodide using a rhodium complex-loaded VP resin catalyst.

The reference numeral 1 denotes a carbonylation reactor which may be, for example, one of those shown in FIGS. 1–3. A liquid product is discharged from the reactor 1 through a line 71. The liquid product contains containing acetic acid and various other components, such as methyl acetate, dimethyl ether, propionic acid, methyl iodide, hydrogen iodide, a rhodium complex and methanol, and has a pressure of in the range of about 15–60. The content of the rhodium complex is generally in the range of 0.02–20 ppm by weight, usually 0.2–5 ppm by weight, in terms of elemental rhodium.

The liquid product is fed to a pressure reducing device 73 such as a pressure reducing valve where the pressure thereof is reduced to about 5 atm or less, preferably 0.5–3 atm. The pressure reduced liquid product is then introduced into a gas separator 75 such as a flasher and is separated into a gas phase and a liquid phase. The gas phase is discharged overhead from the flasher 75 and fed through a line 77 to a distillation device 90, while the liquid phase is discharged from the bottom of the flasher 75 and recycled through lines 79 and 79*b* to the reactor 1. A portion of the liquid phase is diverted from the line 79, fed through a line 79*a* to a heater such as a heat exchanger and recycled to the flasher 75.

A gas product in the reactor 1 is withdrawn overhead through a line 81 and is fed to a scrubber 80. The gas product contains gas components such as CO, $H_2$, methane and $CO_2$ and entrainments such as methyl iodide and methyl acetate. In the scrubber 80, the gas product is brought into counter-current contact with methanol so that the entrainments such as methyl iodide and methyl acetate are collected by the methanol. The entrainment-containing methanol is discharged from the scrubber 80 and is fed through a line 86 to a methanol feed line 82 for the introduction into the reactor 1.

On the other hand, the gas product washed with the methanol is withdrawn overhead from the scrubber 80 and is fed through a line 85 to a pressure control valve 86. The pressure-reduced gas product is then fed to the flasher 75 through the heater 72. Thus, in the flasher 75, the rhodium complex contained in the liquid product is concentrated to 0.03–200 ppm by weight, usually 0.3–50 ppm by weight, in terms of elemental rhodium.

The gas in the line 81 has a very high pressure (for example 42 kg/cm²G) and a temperature of about 40° C. Thus, the gas from the scrubber 80 has also a high pressure and contains a major amount of CO. By introducing the gas from the scrubber 80 into the flasher 75, the partial pressure of CO in the flasher 75 is increased so that the rhodium complex (e.g. RhI₃) contained in the pressure-reduced liquid product in the flasher 75 is prevented from precipitating. Thus, the liquid phase discharged from the flasher 75 through the lines 79 and 79b can be recycled to the reactor without a loss of the rhodium complex. The partial pressure of CO applied to the pressure-reduced liquid product in the flasher 75 is controlled so as to prevent the precipitation of the rhodium complex and is generally in the range of 0.02–3 atm, preferably 0.1–1.5 atm. If desired, the CO-containing gas recovered in the scrubber 80 may be partly or entirely replaced by any other CO containing gas feed such as a fresh CO gas.

In the distillation device 90, the gas phase from the flasher 75 is separated into an acetic acid product fraction recovered through a line 99, a low boiling point top fraction withdrawn through a line 93 and a bottom fraction discharged through a line 95 and recycled to the reactor 1. The top fraction in the line 95 which generally has a pressure of 0.3 kg/cm²G and a temperature of about 15° C. is fed to a scrubber 100 and scrubbed with methanol. The gas scrubbed with methanol is withdrawn overhead from the scrubber 100, while the methanol used in the scrubbing is combined with the methanol from the scrubber 80.

If desired, the distillation device 90 may be constructed by, for example, three, first through third distillation towers connected in series. In the first tower, the gas phase from the flasher 75 is separated into a low boiling point top fraction (fed to the scrubber 100) and a first bottom fraction. The first bottom fraction is fed to the second tower and is separated into water and a second bottom fraction and a product fraction. In the third tower, the second bottom fraction is separated into acetic acid and a heavy fraction which is recycled to the reactor 1.

Figure 4:
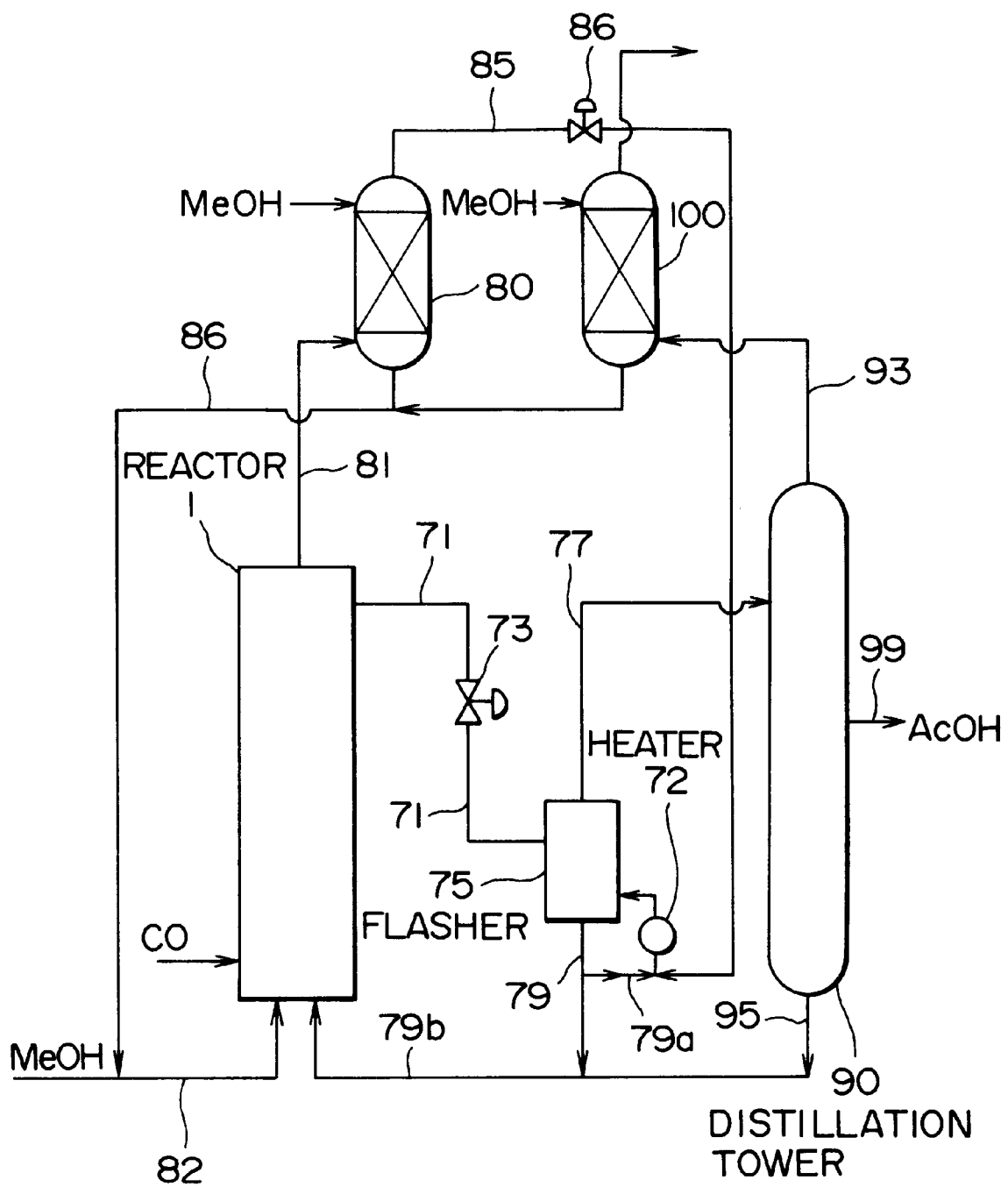
FIGS. 4–7 are each a flow diagram diagrammatically illustrating an apparatus useful for carrying out the process according to the present invention.
Figure 5:
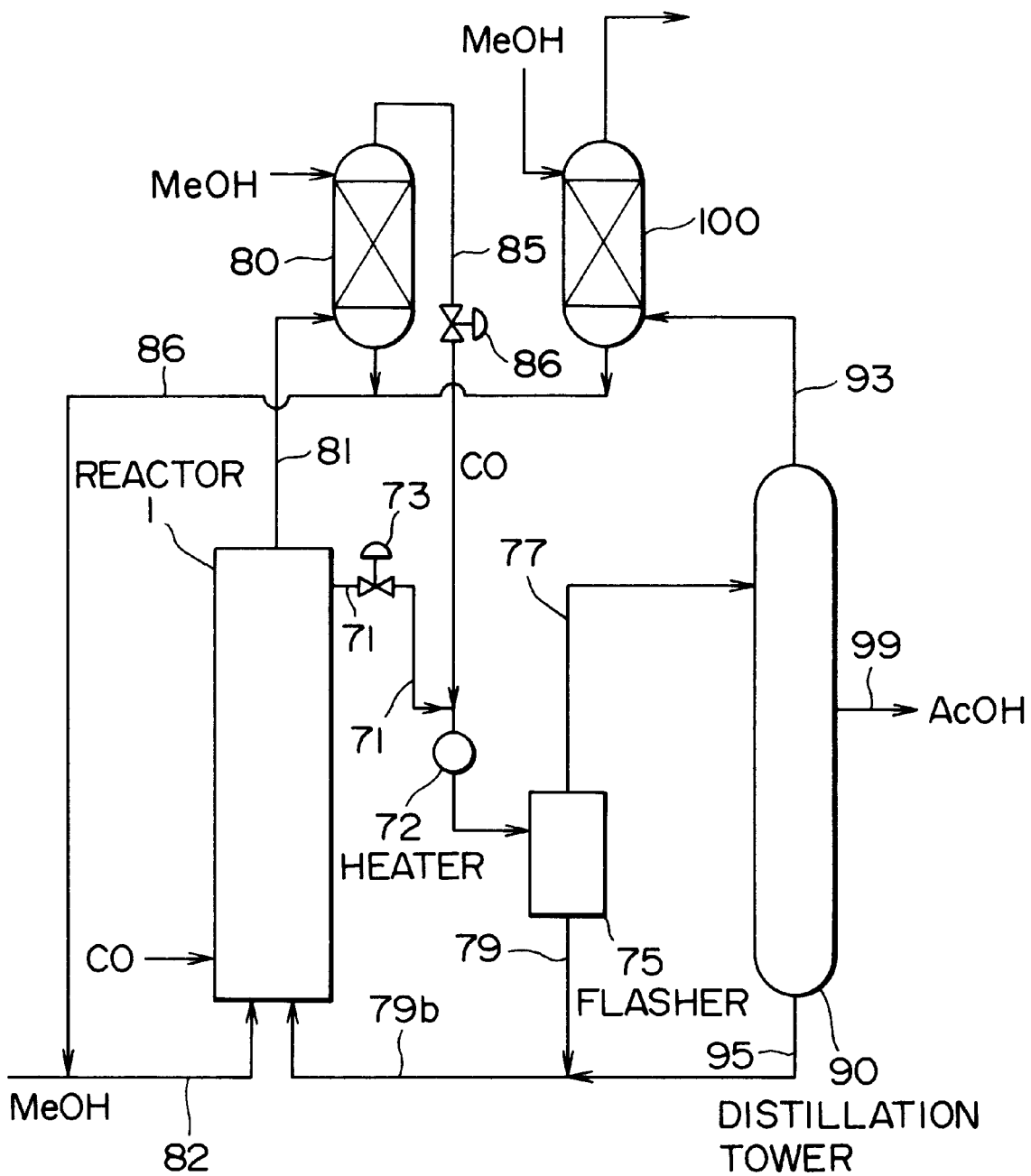

FIG. 5 shows a modified embodiment of the carbonylation apparatus of FIG. 4. In FIG. 5, component parts similar to those of FIG. 4 are designated by the same reference numerals. An acetic acid-containing liquid product is discharged from a reactor 1 through a line 71 and is fed to a pressure reducing valve 73. The pressure-reduced liquid product is then fed to a heater 72 together with a CO-containing gas product withdrawn from a scrubber 80. The mixture of the liquid product and the gas product is introduced into a flasher 75. The other operations are the same as described above with reference to in FIG. 4.

Figure 6:
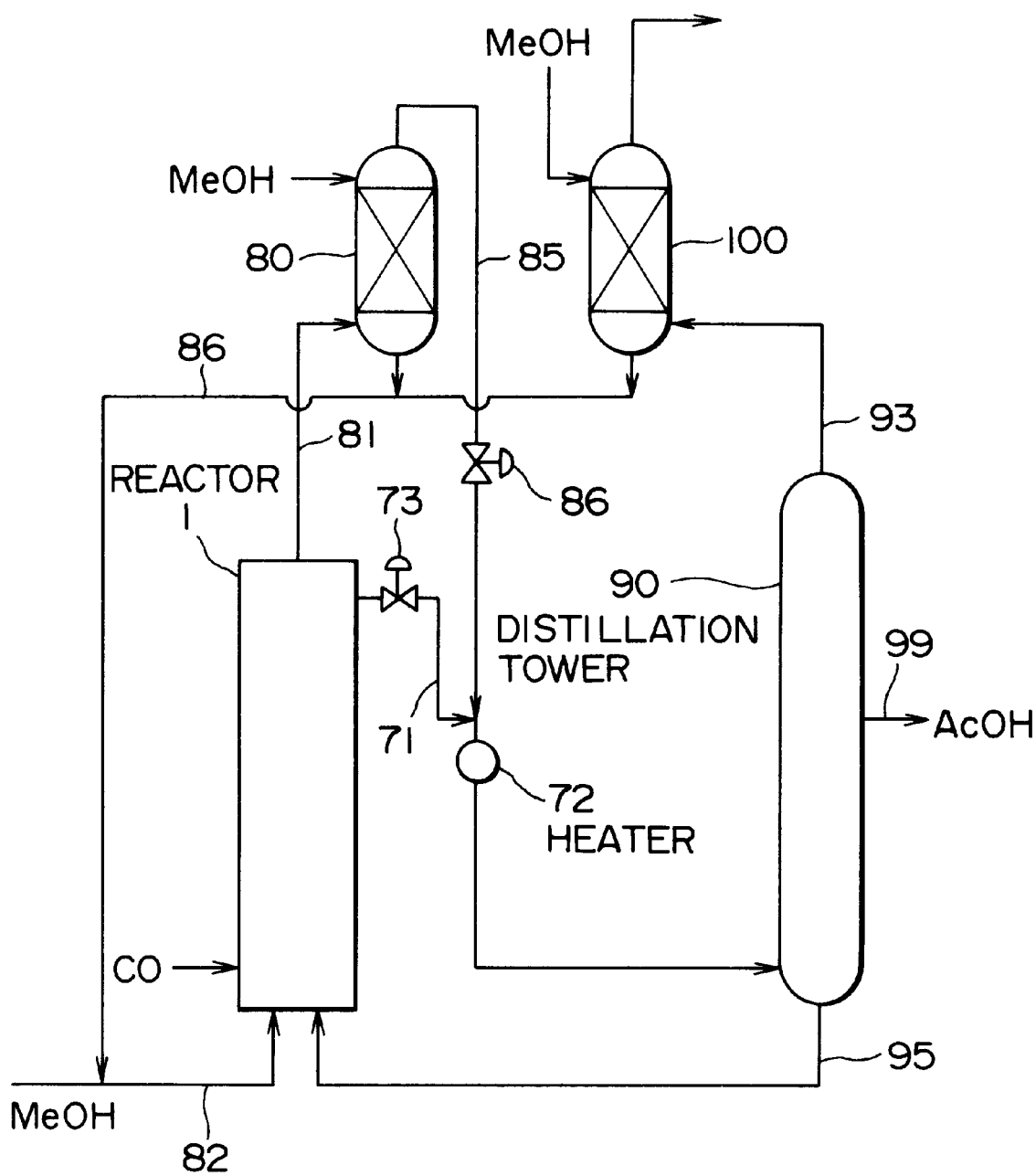

FIG. 6 shows a modified embodiment of the carbonylation apparatus of FIG. 4. In FIG. 6, component parts similar to those of FIG. 4 are designated by the same reference numerals. An acetic acid-containing liquid product is discharged from a reactor 1 through a line 71 and is fed to a pressure reducing valve 73. Similar to the operation of FIG. 5, the pressure-reduced liquid product is then fed to a heater 72 together with a CO-containing gas product withdrawn from a scrubber 80. The mixture of the liquid product and the gas product is directly introduced into a bottom portion of a distillation device 90. The other operations are the same as described above with reference to in FIG. 4.

Figure 7:
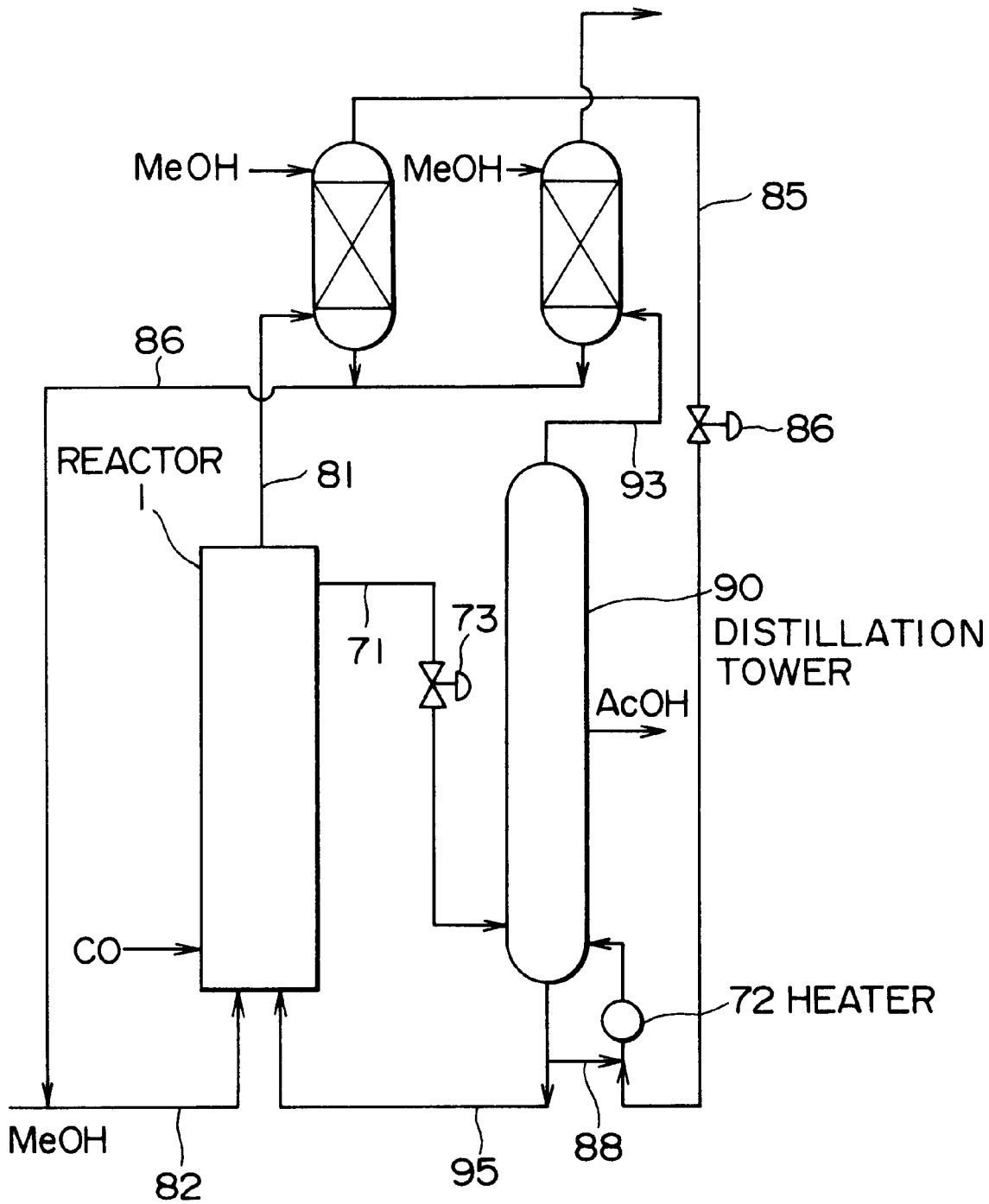

FIG. 7 shows a modified embodiment of the carbonylation apparatus of FIG. 4. In FIG. 7, component parts similar to those of FIG. 4 are designated by the same reference numerals. An acetic acid-containing liquid product is discharged from a reactor 1 through a line 71 and is fed to a pressure reducing valve 73. The pressure-reduced liquid product is fed to a heater 72 and then introduced into a bottom portion of a distillation device 90. A CO-containing gas product withdrawn from a scrubber 80 is to a bottom of the distillation tower 90 through a pressure controlling device 86 and a heater 72. A bottom fraction separated in the distillation device 90 is discharged through a line 95 and recycled to the reactor 1. A portion of the bottom fraction is fed to the heater through a line 88 and recycled to the distillation device 90. The other operations are the same as described above with reference to in FIG. 4.

In the embodiments according to FIGS. 4–7, the rhodium complex discharged from the reactor 1 through the line 71 can be substantially completely recycled to the reactor without a loss thereof, because a CO-containing gas is fed to the liquid product to maintain the partial pressure of CO in the liquid product at a value sufficient to prevent the precipitation of the rhodium complex.

As described previously, the VP resin is unavoidably broken, though slightly, during use, so that pyridine compounds such as pyridine quaternized with methyl iodide are accumulated in the liquid circulating in the reaction system. It has been found that when the content of the pyridine compounds in the reaction liquid within the reactor is in the range of 0.5–200 ppm by weight in terms of elemental nitrogen, the decomposition rate of the VP resin can be minimized while preventing the liberation of the noble metal complex from the VP resin. Especially good results are obtainable when the concentration of the nitrogen compounds is controlled in the range of 3–50 ppm by weight. The control of the nitrogen compound content in the reaction liquid within the reactor may be done by discharging a portion of the reaction liquid to outside of the system.

In the case of the embodiments shown in FIGS. 4–7, for example, a portion of the liquid phase and/or bottom fraction in the lines 78, 95 and/or 79b is continuously or intermittently discharged to maintain the pyridine compound content below a predetermined level. When the pyridine compound content is below the above-specified lower limit, such as in the case of the starting the operation, a quantity of a pyridine compound is added to the reaction mixture in the reactor.

As shown in the formulas (2) and (3), water is produced in situ during the course of carbonylation. It has been found that when the water content in the liquid product is maintained at 10% by weight or less, preferably 1–8% by weight, more preferably 2–5% by weight, the content of hydrogen iodide can be reduced so that the interior surface of the reactor, separation devices (e.g. a flasher and a distillation tower), etc. can be prevented from being corroded, even when titanium or a titanium alloy (e.g. titanium-palladium alloy) which is much less expensive in comparison with zirconium or Hastelloy B is used for the material of the interior surface. When the water content is 10% by weight or less, the hydrogen iodide content can be maintained at 3,000 ppm by weight or less. When the water content is 8% by weight or less, the hydrogen iodide content can be maintained at 500 ppm by weight or less.

It has also been found that when the carbonylation degree Ac of the reaction solution within the reactor (defined hereinbefore) is 0.5–0.9, preferably 0.6–0.8, the corrosion of the reactor, separation devices (e.g. a flasher and a distillation tower), etc. can be effectively prevented while ensuring the satisfactory operation efficiency. The term "carbonylation degree" is defined by the following equation:

$$Ac = (M[CH_3COOH] + M[CH_3COOCH_3] + M[CH_3COOR^1])/$$
$$(M[CH_3COOH] + 2M[CH_3COOCH_3] + 2M[CH_3OCH_3] +$$
$$M[CH_3COOR^1] + M[R^2COOCH_3] + M[CH_3OR^3] + M[CH_3OH])$$

wherein $M[CH_3COOH]$, $M[CH_3COOCH_3]$, $M[CH_3COOR^1]$, $M[CH_3OCH_3]$, $M[R^2COOCH_3]$, $M[CH_3OR^3]$ and $M[CH_3OH]$ represent the amounts, in terms of molarity, of $CH_3COOH$, $CH_3COCCH_3$, $CH_3COOR^1$ where $R^1$ represents an alkyl group having at least two carbon atoms, $CH_3OCH_3$, $R^2COOCH_3$ where $R^2$ represents an alkyl group having at least two carbon atoms, $CH_3OR^3$ where $R^3$ represents an alkyl group having at least two carbon atoms and $CH_3OH$, respectively, which are present in the reaction solution within the reactor.

Even when the water content in the reaction solution within the reactor is the same, the concentration of hydrogen iodide therein varies with the carbonylation degree Ac thereof. When the carbonylation degree is 0.9 or less and when the water content is not greater than 20% by weight, the hydrogen iodide content can be suppressed to 3,000 ppm by weight or less, so that titanium or an alloy thereof can be used as a material of the carbonylation apparatus. When the carbonylation degree is 0.9 or less and when the water content is not greater than 10% by weight, the hydrogen iodide content can be suppressed to 100 ppm by weight or less. Thus, it is preferred that the carbonylation degree of the liquid product fed to a separation zone such as a distillation tower be maintained at not greater than 0.9, for reasons of preventing the corrosion of the interior walls of the separation zone. With an excessively high carbonylation degree of, for example 0.97, the hydrogen iodide content exceeds 3,000 ppm by weight when the water content is higher than 10% by weight, so that the corrosion of a titanium material is caused. The conventional Monsant process, which uses a carbonylation degree of 0.99 and a water content of 15% by weight, cannot utilize an apparatus made of a titanium material.

As described previously, when the water content in the reaction solution is maintained at 10% by weight or less, the hydrogen iodide content in the reaction solution within the reactor can be maintained at 3,000 ppm by weight or less. Thus, the interior surfaces of the reactor, separator, etc. which are in contact with the reaction solution are prevented from being corroded, even when titanium which is much less expensive in comparison with zirconium or Hastelloy B is used for the material of the interior surface. On the other hand, those portions of the interior surfaces of the reactor, separator (e.g. a flasher, a reboiler, a condenser of a distillator), etc. which are not in direct contact with the reaction solution has been found to be exposed to corrosive conditions because of deposition of condensed liquid containing hydrogen iodide. Namely, the alkyl iodide contained in the condensed liquid reacts with hydrogen gas to form hydrogen iodide as follows:

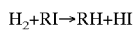

$H_2 + RI \rightarrow RH + HI$

Therefore, when titanium is used as a material for the interior surface of the reactor which is exposed to the gas phase, the exposed portion is corroded.

It has now been found that a titanium/palladium alloy can withstand the chemical attack by hydrogen iodide. Thus, in one preferred embodiment, at least those surfaces of the carbonylation reactor, separator, etc. which are brought into direct contact with a gas phase are formed of a titanium/palladium alloy which is much less expensive than zirconium or Hastelloy B.

Titanium used for forming the reactor, etc. may be those specified in Japanese Industrial Standards JIS 1–3 Classes or a titanium-clad composite such as titanium-clad steel. The thickness of the titanium layer of the composite is generally at least 1 mm, preferably 2–10 mm, more preferably 3–10 mm. The titanium/palladium alloy generally has a palladium content of 0.05–50% by weight, preferably 0.1–0.3% by weight. Titanium/palladium alloys specified in Japanese Industrial Standards JIS 11–13 Classes or a titanium/palladium alloy-clad composite such as titanium/palladium alloy-clad steel. The thickness of the alloy layer of the composite is generally at least 1 mm, preferably 2–10 mm, more preferably 3–10 mm.

In one preferred embodiment, the reactor may be divided into a lower section having a titanium interior surface and an upper section having a titanium/palladium alloy surface. In this case, the liquid level of the reaction solution in the reactor is controlled to position slightly above the interface between the upper and lower sections. Each of the two sections may be provided with a flange so that the two sections may be connected to each other by bolting the flanges which are in abutting engagement with each other. Alternatively, when the two sections are formed of composites, the titanium layer and the alloy layer at end portions are first removed to expose the steel surface. Then, the two sections are abutted and welded together. A spacer is attached to a depressed portion defined by the removed portions. Thereafter, a titanium plate is applied onto the spacer and welded.

It is preferred that the carbonylation be performed while maintaining the hydrogen partial pressure in the range of 0.1–5 kg/cm², more preferably 1–3 kg/cm², for reasons of reducing the amount of impurities in the reaction product such as aldehydes and their derivatives (e.g. acetaldehyde, crotaldehyde, 2-ethylcrotaldehyde, propionic acid and ethyl acetate) and iodides (e.g. ethyl iodide, propyl iodide, butyl iodide, pentyl iodide and hexyl iodide). These impurities are difficult to separate from the desired reaction product such as acetic acid. By controlling the hydrogen partial pressure as above, the formation of such impurities can be minimized.

A raw material CO feed generally contains hydrogen. Hydrogen is also produced in situ during the carbonylation reaction. Thus, the hydrogen partial pressure may be controlled within the above range by discharging part of the gas phase in the reactor out of the system through, for example, a pressure reducing valve and/or by adjusting the amount of hydrogen contained in the raw material CO feed.

Among the above impurities, aldehyde condensation products, such as crotaldehyde and 2-ethyl crotaldehyde, having an unsaturated bond show a reducing power and, hence, adversely affect the permanganate time of the desired carbonyl product. The permanganate time represents an index for a total amount of reducing substances contained in the product. In the case of a carboxylic acid, such as acetic acid, the permanganate time thereof is desirably at least 120 minutes, more preferably at least 240 minutes.

In addition to the hydrogen partial pressure, the amount of hydrogen iodide in the reaction mixture also has an influence upon the aldehyde content in the carbonylation product. The amount of the aldehyde and derivatives thereof in the reaction solution within the reactor is preferably 3,000 ppm by weight or less, more preferably 1,500 ppm by weight or less.

The content of the iodide impurities is influenced by the hydrogen partial pressure, hydrogen iodide content and alkali metal iodide content in the reactor. The iodide impurity content decreases with a decrease of the hydrogen partial pressure and with a decrease of the hydrogen iodide content and the alkali metal iodide content. The hydrogen iodide content is preferably 100 ppm by weight or less, more preferably 50 ppm by weight or less.

The aldehydes and iodides are considered to be produced through the following reaction routes:

$$CH_3COOH + H_2 \rightarrow CH_3CHO + H_2O \tag{1}$$

$$CH_3CHO + H_2 \rightarrow CH_3CH_2OH \tag{2}$$

$$CH_3CH_2OH + HI \rightarrow CH_3CH_2I + H_2O \tag{3}$$

$$CH_3CH_2I + CO \rightarrow CH_3CH_2COI \tag{4}$$

$$CH_3CH_2COI + H_2O \rightarrow CH_3CH_2COOH + HI \tag{5}$$

$$2CH_3CHO \rightarrow CH_3CH{=}CHCHO \text{ (crotaldehyde)} + H_2 \tag{6}$$

$$CH_3CH{=}CHCHO + CH_3CHO \rightarrow CH_3CH{=}C(C_2H_5)CHO + H_2O \tag{7}$$

$$CH_3CH_2OH + CH_3COOH \rightarrow CH_3COOCH_2CH_2CH_2OH + H_2O \tag{8}$$

$$CH_3CH{=}CHCHO + 2H_2 \rightarrow CH_3CH_2CH_2CH_2OH \tag{9}$$

$$CH_3CH_2CH_2CH_2OH + HI \rightarrow CH_3CH_2CH_2CH_2I + H_2O \tag{10}$$

The reactions (1) and (2) above can be inhibited by controlling the hydrogen partial pressure below 5 kg/cm$^2$. The reaction (3) can be inhibited by maintaining the HI content in the reaction solution within the reactor at 100 ppm by weight or less. The control of the HI content can also inhibit the reactions (4), (5) and (8). By controlling the hydrogen partial pressure below 5 kg/cm$^2$, the reactions (6), (7), (9) and (10) can be restrained. The reactions (3) and (10) are promoted not only by HI but also alkali metal iodides such as LiI and NaI. A process is known in which acetic acid is produced by carbonylation of methanol in the presence of a small amount of water while adding a large amount (e.g. 50,000–100,000 ppm by weight) of an alkali metal iodide. This process has a problem because of the production of a large amount of organic iodides as understood from the above reaction schemes. According to the above preferred embodiment, it is possible to produce crude acetic acid containing only a very small amount of organic iodide impurities.

Figure 9:
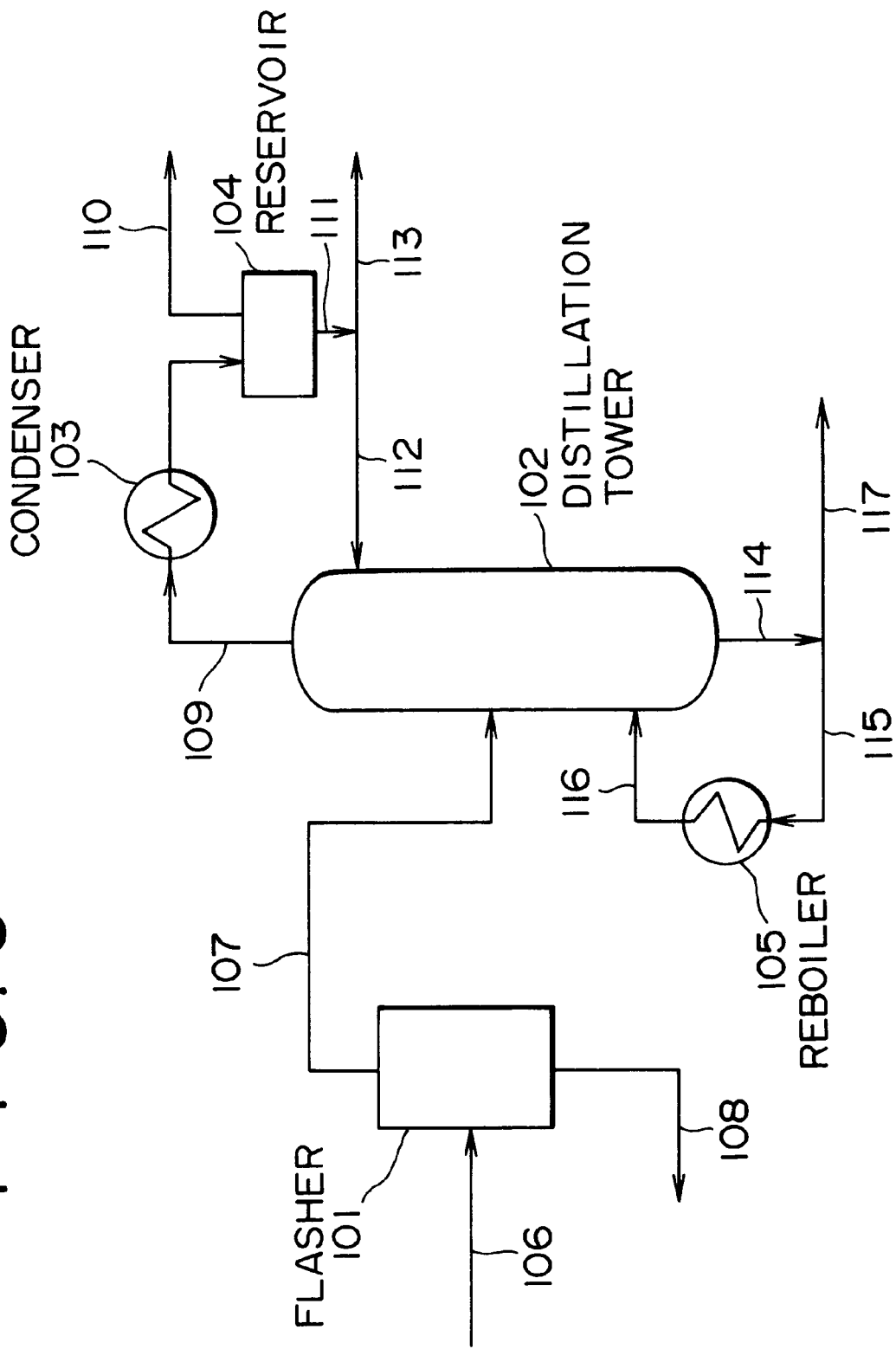
FIG. 9 is a flow diagram diagrammatically illustrating a distillation step of the process according to the present invention.

One preferred distillation step according to the present invention will now be described with reference to FIG. 9, in which designated as 101 is a flasher, 102 a distillation tower, 103 a condenser, 104 a condensed liquid reservoir and 105 is a reboiler. A liquid product discharged from a carbonylation reactor (not shown) is introduced into the flasher 101 and is separated into a gas phase containing acetic acid and a liquid phase. The gas phase is discharged overhead from the flasher 101 and fed through a line 107 to the distillation tower 102, while the liquid phase is discharged from the bottom of the flasher 101 and recycled through a line 108 to the reactor.

In the distillation tower 102, a top fraction is discharged through a line 109 and is fed to the condenser 103 to form a gas-liquid mixture which is collected in the reservoir 104. The non-condensed gas is withdrawn from the reservoir 104 through a line 110, while the condensed liquid is discharged from the reservoir 104 through a line 111. A part of the discharged liquid is recycled to an upper portion of the distillation tower 102 through a line 112, with the remainder part being recycled through a line 113 to the reactor. The liquid in the line 113 is a light fraction separated from the crude acetic acid product and containing methyl iodide, methyl acetate, water, acetic acid, hydrogen iodide, etc.

A portion of the bottom fraction discharged from the distillation tower 102 through a line 114 is introduced into the reboiler 105 and recycled to a lower portion of the distillation tower 102, with the remainder of the bottom fraction being fed to a second distillation tower to obtain refined acetic acid. The water content of the bottom fraction in the line 117 is preferably 1% by weight or less, more preferably 0.2% by weight or less.

By maintaining the water content in the liquid product discharged through the line 106 at 10% by weight or less, the HI content can be maintained at 3,000 ppm by weight or less. Thus, it is possible to use the flasher 101 and the distillation tower 102 the interior surfaces of which are formed of titanium or a titanium-palladium alloy. In particular, since there is established an equilibrium between HI, water, methyl iodide, methanol, acetic acid, methyl acetate, etc. in the flasher 101, the concentration of HI cannot be so high as to cause the corrosion of the interior wall of titanium.

In the top portion of the distillation tower 102, the water content may exceed 10% by weight. However, since the light fraction in the tower top portion contains methanol and methyl acetate, the carbonylation degree Ac is not greater than 0.9. Thus, since the HI content is not greater than 3,000 ppm by weight, it is possible to use titanium as the material of the interior surface of the top portion of the distillation tower 102.

In the condenser 103, local concentration of HI is apt to occur. In the reboiler 105, the heated wall may cause the concentration of HI. Thus, it is preferred that at least the interior surfaces of the condenser 103 and the reboiler 105 be made of a titanium-palladium alloy. Further, it is advisable to use a titanium-palladium alloy in portions of the interior wall surfaces at which corrosion is apt to occur, such as distillation plates having a complicated shape, flasher internals and packings.

The conditions under which the flasher 101 and the distillation tower 102 are operated may vary according to the compositions of the liquid product and the gas phase. Generally, a temperature of 80–180° C. and a pressure of from a reduced pressure to 5 atm are used.

The distillation step may be performed using three distillation towers, i.e. successively a first low boiling tower, a second water-removing tower and a third high boiling tower. In the first tower, methyl iodide, methyl acetate, etc. are removed. In the second tower, water is removed. In the third tower, high boiling components such as propionic acid are separated to obtain high purity acetic acid. Preferably, however, a combination of two, first and second towers is used in the present invention. In this case, the first tower performs the removal of a low boiling fraction as well as water, while the second tower removes high boiling components. More preferably, the distillation is carried out using a single distillation tower for collecting the desired carbonylated product such as acetic acid.

Figure 10:
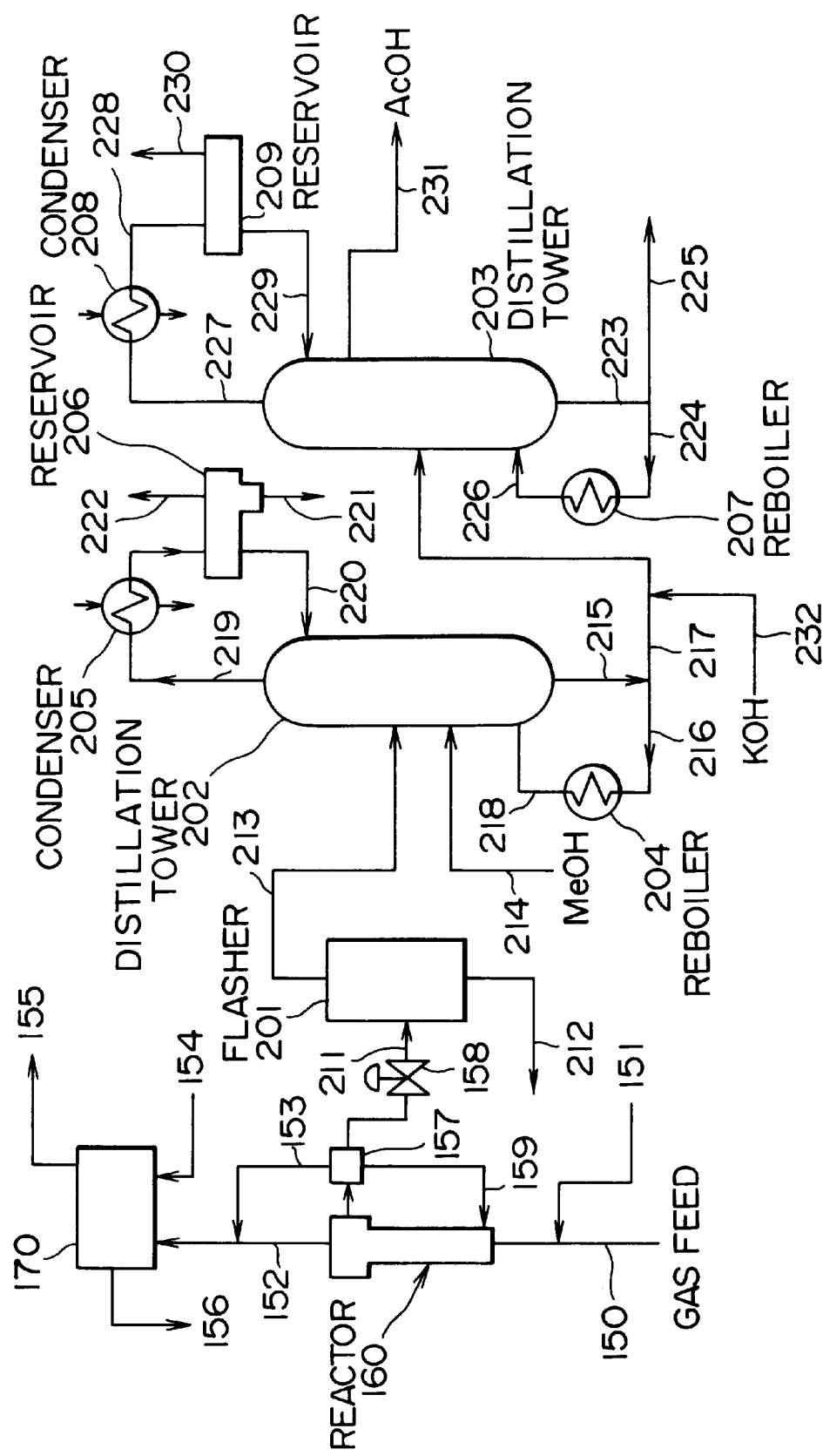
FIGS. 10 and 11 are each a flow diagram diagrammatically illustrating an apparatus useful for carrying out the process according to the present invention.

FIG. 10 illustrates a flow chart of a preferred carbonylation apparatus for carrying out the process of the present invention. Designated as 160 is a bubbling-type reactor, 170 is a low boiling point matter recovering device, 201 is a flasher, 202 and 203 are first and second distillation towers, 204 and 207 are first and second reboilers, 205 and 208 are first and second condensers and 206 and 209 are first and second reservoirs. A raw material feed containing methanol and CO is fed through a line 150 to the reactor 160, where the methanol and CO are reacted in the presence of noble metal complex-bearing VP resin catalyst and methyl iodide.

The gas product in the reactor 160 is withdrawn overhead through a line 152 and is fed to the recovering device 170 for recovering low boiling point matters such as methyl iodide and methyl acetate. The recovered material is recycled through a line 156 to the reactor 160. Non-recovered gas containing CO, $H_2$, methane and $CO_2$ is withdrawn from the recovering device 170 through a line 155.

The liquid product in the reactor 160 is fed to a gas-liquid separator 157 (e.g. a reservoir) for the separation of a gas phase. The gas phase is fed through a line 153 to the recovering device 170. A portion of the liquid product from which a gas is separated is returned to the reactor 160 through a line 159 with the remainder portion being fed to a pressure reducing valve 158 and then to the flasher 201 for the separation into a gas phase and a liquid phase. The gas phase is discharged overhead from the flasher 201 and fed through a line 213 to the first distillation tower 202, while the liquid phase is discharged from the bottom of the flasher 202 and recycled through lines 212 and 151 to the reactor 160.

In the first distillation tower 202, the gas phase from the flasher 201 is separated into a first top fraction and a first bottom fraction. The first top fraction is discharged through a line 219 and is fed to the condenser 205 to form a gas-liquid mixture which is collected in the reservoir 206. The non-condensed gas is withdrawn from the reservoir 206 through a line 222 and is recycled to the recovering device 170 through a line 154. A portion of the condensed liquid is discharged from the reservoir 206 through a line 221 and is recycled to the reactor 160 through the line 151. The remainder portion of the condensed liquid is recycled to an upper portion of the first distillation tower 202 through a line 220.

The liquid flowing through the line 221 contains methyl iodide, methyl acetate, water, acetic acid, etc.

A portion of the bottom fraction (an organic carboxylic acid fraction) discharged from the first distillation tower 202 through a line 215 is introduced into and heated in the first reboiler 204 and recycled to a lower portion of the first distillation tower 202, with the remainder of the bottom fraction being fed to the second distillation tower 203. The bottom fraction in the line 217 is crude acetic acid product which has a water content of at least 0.3% by weight or less and from which most of the iodides have been removed.

In the second distillation tower 203, the first bottom fraction from the first distillation tower 202 is separated into a second top fraction, a product fraction and a second bottom fraction. The second top fraction is discharged through a line 227 and is fed to the second condenser 208 to form a gas-liquid mixture which is collected in the second reservoir 209. The non-condensed gas is withdrawn from the reservoir 209 through a line 230 and is recycled to the recovering device 170 through a line 154, while the condensed liquid is recycled to an upper portion of the second distillation tower 203 through a line 229.

A portion of the second bottom fraction (an organic carboxylic acid fraction) discharged from the second distillation tower 203 through a line 223 is introduced into and heated in the first reboiler 207 and recycled to a lower portion of the second distillation tower 203, with the remainder of the bottom fraction being recovered through a line 225.

The product fraction (e.g. acetic acid) is discharged through a line 231 for recovery. The acetic acid recovered has a water content of not greater than 0.1% by weight, a propionic acid content of not greater than 500 ppm by weight, a permanganate time (measured with potassium permanganate) of at least 120 minutes, preferably at least 240 minutes and an iodine content of not greater than 20 ppb by weight. If desired, the acetic acid thus produced may be treated with a macroporous strong acid ion exchanger of Ag ion type for the complete removal of iodine according to a method disclosed, for example, in JP-B-H5-21031.

If desired, methanol may be fed to a lower portion of the first distillation tower 202 through a line 214 to reduce the hydrogen iodide content by the following reaction:

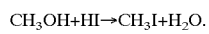

$$CH_3OH + HI \rightarrow CH_3I + H_2O.$$

If desired, a small amount of a KOH aqueous solution may be fed to the second distillation tower 203 through a line 232 to remove iodine ion as KI through the line 225.

According to the process shown in FIG. 10, the bottom fraction in the first distillation tower 202 has a hydrogen iodide content of generally 500 ppb by weight or less, preferably 100 ppb by weight or less, a water content of generally 3,000 ppm by weight or less, preferably 1,000 ppm by weight or less and an aldehyde derivative content of generally 10 ppm by weight or less, preferably 5 ppm by weight of less.

Since the liquid product supplied to the separation zone has minimized metal corrosive properties, it is not necessary to use a highly anti-corrosion material as the interior walls of the flasher 201 and the distillation tower 202. Thus, titanium or a titanium-palladium alloy can be used for the flasher 201 and distillation tower 202. Also the interior walls of the reboiler 204, condenser 205 and reservoir 206 may be formed of titanium or a titanium-palladium alloy. Since the bottom fraction from the first distillation tower 202 has further less metal corrosive properties, ordinary stainless steel may be used for the second distillation tower 203 and associated devices thereof.

In the embodiment of FIG. 10, the liquid product from the reactor 160 is subjected to the treatment in the flasher 201 before introduction to the distillation tower 202. However, the pretreatment with the flasher 201 may be omitted if desired. In such a case, a middle fraction is discharged at a position below the point at which methanol is fed through the line 214 and is fed to the second distillation tower 203, while the first bottom fraction from the first distillation tower 202 is recycled to the reactor 160.

Figure 11:
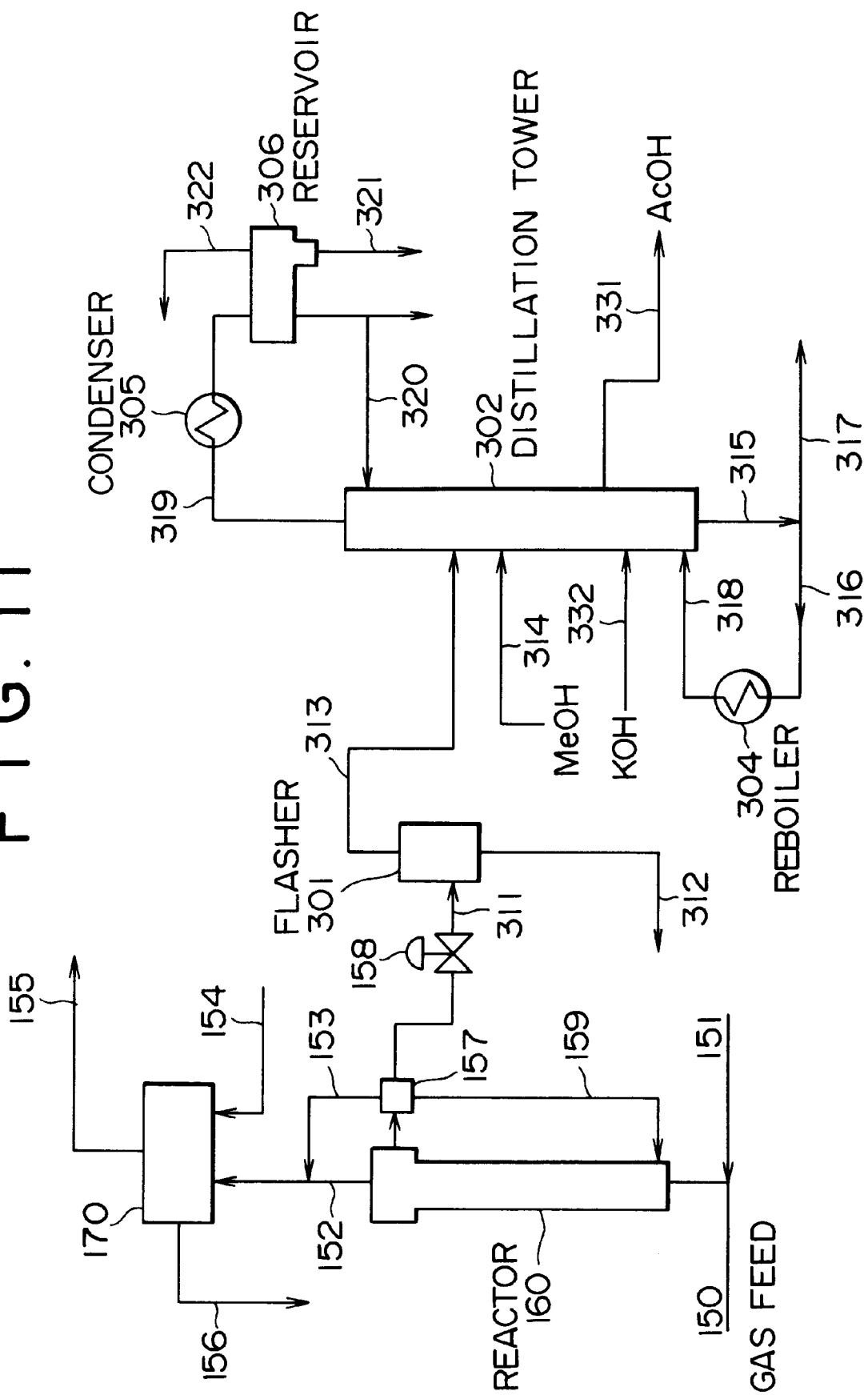

FIG. 11 shows a further embodiment according to the present invention, in which the same reference numerals as those in FIG. 10 designate the similar component parts. The liquid product from the reactor 160 is fed to a flasher 301 through a line 311 and a gas phase is fed through a line 313 to a distillation tower 302. A liquid phase is recycled to the reactor 160. A light fraction containing methyl iodide, methyl acetate, water and acetic acid is topped from the distillation tower 302 through a line 319 and is condensed in a condenser 305 and collected in a reservoir 306. The non-condensed gas is withdrawn through a line 322, while a portion of the condensed liquid is discharged through lines 321 and recycled to the reactor 160. Another portion of the liquid is returned to the distillation tower 302 through a line 320. Methanol and a KOH aqueous solution are fed to the distillation tower 302 through lines 314 and 332, respectively. A bottom fraction is discharged through a line 315 and a portion thereof is recycled through a line 316, a reboiler 304 and a line 318, with the remainder portion being recovered.

An acetic acid product fraction is discharged through a line 331. The acetic acid recovered has a water content of not greater than 0.3% by weight, preferably not greater than 0.1% by weight, a propionic acid content of not greater than 500 ppm by weight, preferably not greater than 100 ppm by weight, a permanganate time (measured with potassium permanganate) of at least 120 minutes, preferably at least 240 minutes and an iodine content of not greater than 100 ppb by weight, preferably not greater than 20 ppb by weight. If desired, the acetic acid thus produced may be treated with a macroporous strong acid ion exchanger of Ag ion type for the complete removal of iodine.

The following examples will further illustrate the present invention.

EXAMPLE 1

105 Grams (dry weight: 67 g) of crosslinked poly-4-vinylpyridine/divinyl benzene copolymer resin having a crosslinking degree of 60%, a nitrogen content of 6.1% by weight, a pore volume of 0.32 cc/g, an average pore diameter of 21 nm and an average particle diameter of 0.43 mm was immersed in methanol, to which 1,400 g of a mixed solution containing 8% by weight of methyl iodide, 45% by weight of methanol and 47% by weight of acetic acid were added. The mixture was then charged in a 2,500 cc autoclave made of titanium together with 1.4 g of $RhCl_3 \cdot 3H_2O$. After deaeration with carbon monoxide gas, the mixture was heated to 190° C. Then, carbon monoxide was fed to the autoclave through an autogeneous pressure control valve so that the pressure within the autoclave showed 50 kg/cm² (initial partial pressure of carbon monoxide: 15 kg/cm²). The mixture within the autoclave was reacted for 1 hour. Then the autoclave was cooled to room temperature and was purged with nitrogen gas. The supernatant was removed by decantation and the solids were washed several times with methanol to obtain a rhodium-loaded polymer catalyst having a Rh content of 0.8% by weight. The rhodium complex is an anion having the formula $[RhCO_2I_2]^-$.

Figure 8:
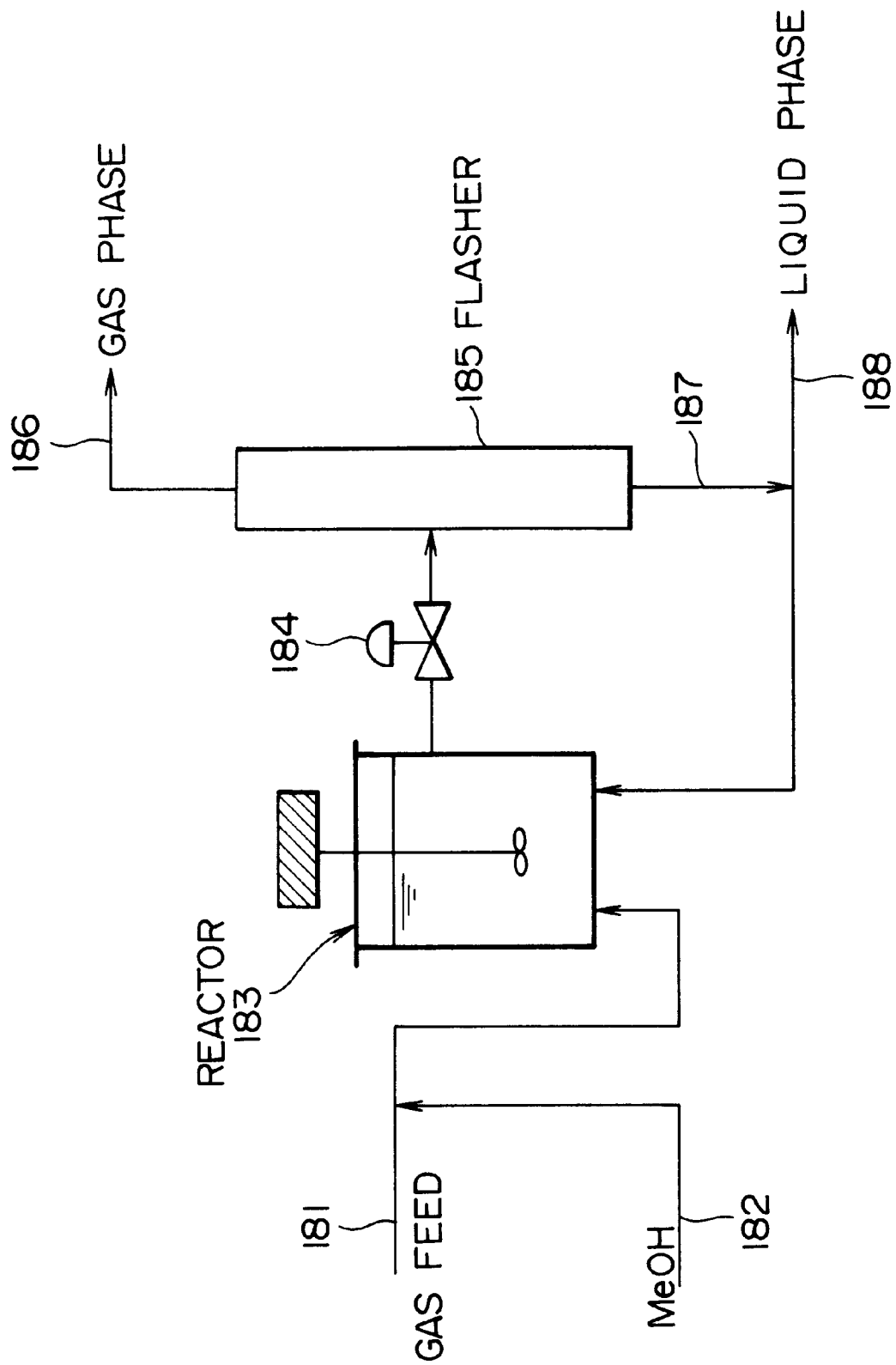
FIG. 8 is a flow diagram diagrammatically illustrating an acetic acid preparation apparatus used in Example.

Using the thus obtained catalyst, acetic acid was produced with an apparatus as shown in FIG. 8. In a 2,500 ml autoclave 183 made of titanium and equipped with a stirrer was charged the above rhodium catalyst. A mixed gas of CO and $H_2$ (feed ratio 99:1) and methanol were fed to the autoclave 183 through lines 181 and 182, respectively, and the carbonylation was carried out at a temperature of 180° C. and a pressure of 40 kg/cm²G. The reaction mixture (liquid product) was discharged at a rate of 1,000 ml/hour from the autoclave 183 and fed through a pressure controlling valve 184 to a flasher 185 operated at 125° C. and 2.3 atm. In the flasher 185, the liquid product was separated into a gas phase and a liquid phase. The gas phase was withdrawn through a line 186 at a rate of 330 ml/hour, while the liquid phase was discharged from the flasher 185 through a line 187 at a rate of 670 ml/hour. A portion of the liquid phase was extracted through a line 188 at a rate of 2 ml/hour to control the pyridine compound concentration in the reaction mixture within the autoclave 183, with the remainder portion being recycled to the autoclave 183.

The nitrogen concentration in the liquid product increased in the initial stage but became constant. The composition of the liquid product 500 hours after the initiation of the continuous reaction are as follows:

| | |
|---|---|
| Methyl iodide: | 14.0% by weight |
| Methanol: | 0.2% by weight |
| Methyl acetate: | 25.8% by weight |
| Acetic acid: | 60.0% by weight |
| Pyridine compounds (in terms of N): | 15 ppm by weight |
| Rhodium: | 1.8 ppm by weight. |

The pyridine compound content (in terms of N) of the solution extracted through the line 188 was 22 ppm by weight. The pyridine compound content was measured by chemical luminescence method, while the Rh content was measured by atomic absorption method. The catalyst has a pyridine compound content of 4.0 g (67 g×6.1%). The pyridine compound content in the extracted solution is $44 \times 10^{-6}$ g/hour (2 ml/hour×22 ppm by weight). Thus, the decomposition rate of the rhodium-loaded VP resin catalyst is $11 \times 10^{-4}$% by weight/hour.

EXAMPLE 2

Example 1 was repeated in the same manner as described except that the liquid phase was extracted through the line 188 at a rate of 4.4 ml/hour so that the pyridine compound concentration in the reaction mixture within the autoclave 183 was 7 ppm by weight.

EXAMPLE 3

Example 1 was repeated in the same manner as described except that the liquid phase was extracted through the line 188 at a rate of 44 ml/hour so that the pyridine compound concentration in the reaction mixture within the autoclave 183 was 0.8 ppm by weight.

EXAMPLE 4

Example 1 was repeated in the same manner as described except that the liquid phase was extracted through the line 188 at a rate of 0.5 ml/hour so that the pyridine compound concentration in the reaction mixture within the autoclave 183 was 60 ppm by weight.

EXAMPLE 5

Example 1 was repeated in the same manner as described except that the liquid phase was extracted through the line 188 at a rate of 0.2 ml/hour so that the pyridine compound concentration in the reaction mixture within the autoclave 183 was 150 ppm by weight.

COMPARATIVE EXAMPLE 1

Example 1 was repeated in the same manner as described except that the liquid phase was extracted through the line 188 at a rate of 200 ml/hour so that the pyridine compound concentration in the reaction mixture within the autoclave 183 was 0.3 ppm by weight.

COMPARATIVE EXAMPLE 2

Example 1 was repeated in the same manner as described except that the liquid phase was extracted through the line 188 at a rate of 0.1 ml/hour so that the pyridine compound concentration in the reaction mixture within the autoclave 183 was 250 ppm by weight.

The decomposition rate of the rhodium-loaded VP resin catalyst and the rhodium liberation in each of the above Examples and Comparative Examples are summarized in Table 1.

TABLE 1

| Example No. | Nitrogen Content (wt.ppm) | VP Resin Decomposition Rate (wt %/hour) | Rhodium Liberation Amount (wt.ppm) |
|---|---|---|---|
| 1 | 15 | $11 \times 10^{-4}$ | 1.8 |
| 2 | 7 | $11 \times 10^{-4}$ | 1.0 |
| 3 | 0.8 | $13 \times 10^{-4}$ | 0.4 |
| 4 | 60 | $11 \times 10^{-4}$ | 14.0 |

TABLE 1-continued

| Example No. | Nitrogen Content (wt.ppm) | VP Resin Decomposition Rate (wt %/hour) | Rhodium Liberation Amount (wt.ppm) |
|---|---|---|---|
| 5 | 150 | $10 \times 10^{-4}$ | 1.8 |
| Comp. 1 | 0.3 | $23 \times 10^{-4}$ | 0.4 |
| Comp. 2 | 250 | $10 \times 10^{-4}$ | 30.0 |

From the results shown in Table 1, it will be appreciated that when the pyridine compound concentration in the reaction mixture within the autoclave is maintained in the range of 0.5–200 ppm by weight, the VP resin decomposition rate can be reduced while reducing the rhodium liberation.

EXAMPLE 6

Test 1

Titanium was tested for the anti-corrosion resistance to a boiling aqueous HI solution. An aqueous HI solution was placed in a glass vessel and deaerated with a nitrogen gas. The solution was then heated for boiling. A titanium test piece was immersed in the boiling solution and maintained as such for 96 hours. The above test was repeated using HI solutions having various HI concentrations. The corrosion resistance and the corrosion speed were evaluated and the results are summarized in Table 2.

TABLE 2

| HI concentration (wt.ppm) | 8,500 | 1,200 | 600 |
|---|---|---|---|
| Corrosion Resistance | no good | good | good |
| Corrosion Speed (mm/year) | 0.23 | 0.00 | <0.01 |

Test 2

Test 1 was repeated in the same manner as described except that a mixed HI-water-acetic acid solution having a HI concentration shown in Table 3, a water content of 5% by weight and an acetic acid concentration of 95% by weight was substituted for the aqueous HI solution. The results are shown in Table 3.

TABLE 3

| HI concentration (wt.ppm) | 6,000 | 1,200 | 600 | 6,000* |
|---|---|---|---|---|
| Corrosion Resistance | good | good | good | good |
| Corrosion Speed (mm/year) | <0.01 | <0.01 | 0.00 | 0.00 |

*: Test was carried out at 80° C. (not boiling)

Test 3

Test 2 was repeated in the same manner as described except that a titanium-palladium alloy test piece was substituted for the titanium test piece. The results are shown in Table 4.

TABLE 4

| HI concentration (wt.ppm) | 6,000 | 1,200 | 200 | 6,000* |
|---|---|---|---|---|
| Corrosion Resistance | good | good | good | good |
| Corrosion Speed (mm/year) | <0.01 | 0.00 | 0.00 | 0.00 |

*: Test was carried out at 80° C. (not boiling)

Test 4

Test 2 was repeated in the same manner as described except that a Hastelloy B test piece was substituted for the titanium test piece. The results are shown in Table 5.

TABLE 5

| HI concentration (wt.ppm) | 6,000 | 1,200 | 200 | 6,000* |
|---|---|---|---|---|
| Corrosion Resistance | good | good | good | good |
| Corrosion Speed (mm/year) | 0.02 | 0.03 | 0.08 | 0.02 |

*: Test was carried out at 80° C. (not boiling)

Test 5

The conditions A and B shown in Table 6 were each established in a glass vessel. The conditions A and B correspond to those in a bottom of a distillation tower and those in a top of the distillation tower, respectively. A titanium test piece and a titanium-palladium alloy test piece were each placed in respective glass vessels such that a part thereof was located above the liquid level. The space above the liquid level was pressurized with CO. Each of the test pieces was maintained for 336 hours in the corresponding glass vessel.

TABLE 6

| Condition | A | B |
|---|---|---|
| Temperature (° C.) | 142 | 104 |
| Pressure (atm) | 2.3 | 2.1 |
| Hydrogen Iodide (wt.ppm) | 406 | 17.3 |
| Water (wt. %) | 3.3 | 13.2 |
| Acetic acid (wt. %) | 96.4 | 67.6 |
| Methyl iodide (wt. %) | 0.4 | 2.1 |
| Methyl acetate (wt. %) | 0.1 | 17.0 |
| Methanol (wt. %) | 0.0 | 0.8 |
| Carbonylation degree (mol/mol) | 0.999 | 0.840 |

Each of the test pieces was found to have good corrosion resistance and to show corrosion speed of 0.00 mm/hour. Similar test was performed using bent test samples to reveal that good corrosion resistance and corrosion speed of 0.00 mm/hour were obtainable.

Test 6

Similar tests were also performed using, as test samples, a titanium test piece and a titanium-palladium test piece each sandwiched between polytetrafluoroethylene plates such as to form a small gap between them. With the condition A, the titanium test piece showed partial corrosion and a corrosion speed of <0.01 mm/year, while the titanium-palladium alloy showed good corrosion resistance and a corrosion speed of 0.00 mm/year. With the condition B, the titanium test piece showed good corrosion resistance and a corrosion speed of 0.00 mm/year.

From the results of the above tests, it is confirmed that titanium and a titanium-palladium alloy can be suitably used as a material for a distillation tower or other devices which are brought into contact with carbonylation reaction liquid, such as a flasher, a condenser and reboiler.

EXAMPLE 7

A supported rhodium catalyst was prepared as follows. A 4-vinylpyridine-divinylbenzene resin (cross-linking degree: 59%; 6.7 g (on dry basis)) was swelled well with methanol and charged in a 250 ml autoclave, having an interior surface of titanium and equipped with a stirring blade, together with 140 g of a solution consisting of 45% by weight of methanol, 47% by weight of acetic acid and 8% by weight of methyl iodide and 0.18 g of rhodium acetate. After deaeration several times with 50 kg/cm$^2$G nitrogen, the autoclave was heated to 190° C. Then, carbon monoxide was charged into the autoclave through an automatic pressure control valve until a total pressure of 50 kg/cm² resulted (initial carbon monoxide partial pressure: 150 kg/cm²). After 30 minutes reaction, the autoclave was cooled and purged with nitrogen gas. The supernatant was removed by decantation and the solids were washed several times with methanol to obtain a rhodium-loaded resin catalyst. The atomic absorption analysis and gas chromatography of the supernatant revealed that the catalyst had a Rh content of 0.9% based on the weight of the resin and an iodine content of about 1 equivalent per one pyridine ring.

In a 100 ml autoclave equipped with a stirrer were placed 5 g of the thus obtained Rh-loaded catalyst (dry basis), to which a liquid raw material feed containing methanol, methyl iodide, acetic acid and methyl acetate was continuously fed by a pump and a control amount of a gas feed containing CO and $H_2$ was continuously fed by a mass flow controller, thereby to perform the carbonylation of methanol at a temperature of 180° C. and a pressure of 40 kg/cm² G. The water partial pressure was 2 atm. In the inlet portion of the autoclave, the methyl iodide concentration was 17% by weight and the carbonylation degree was 0.4. In the outlet portion of the autoclave, the methyl iodide concentration was 14% by weight, the carbonylation degree was 0.8 and the water concentration was 5.5% by weight.

The liquid product discharged from the autoclave was introduced into a pressure reducing valve so that the pressure was reduced to 2.4 atm. The pressure-reduced is liquid product was then fed to a flasher and subjected to a liquid-gas separation at 140° C. The liquid phase was recycled by a pump to the autoclave, while the gas phase was cooled to 20° C. with a cooler to obtain a condensate and a gas. The condensate was recovered in a reservoir. The pressure reducing valve, flasher, cooler and reservoir were made of titanium.

The above operation was continued for 7,000 hours. The catalyst was found to show unchanged catalytic activity throughout the continuous operation. No corrosion of the autoclave, flasher, reducing valve, cooler and reservoir was observed and no deposition of scales on the interior wall thereof was observed.

The recovered condensate was distilled with a batch type glass distillation column to obtain acetic acid. When a stainless steel packing was used, corrosion thereof occurred. No corrosion was observed when a titanium packing material was used.

EXAMPLE 8

Carbonylation of methanol was carried out using the apparatus shown in FIG. 10. The operation conditions were as follows:

Reactor 160:
  Inside wall:
  Inside wall beneath the liquid level: Ti
  Inside wall above the liquid level: Ti—Pd alloy
  Catalyst:
  Rh-loaded VP resin (Rh content: 0.8 wt. %)
  Reaction conditions:
  Temperature: 180° C.
  CO partial pressure: 20 kg/cm²
  $H_2$ partial pressure: 0.25 kg/cm²

Line 211:
  Composition of pressure reduced liquid product:
  Carbonylation degree: 0.76

| | |
|---|---|
| Methyl iodide: | 14.0 wt. % |
| Methanol: | 1.9 wt. % |
| Acetic acid: | 53.4 wt. % |
| Methyl acetate: | 23.7 wt. % |
| Water: | 7 wt. % |
| Hydrogen iodide: | 25 wt. ppm |
| Acetaldehyde: | 80 wt. ppm |
| Propionic acid: | 32 wt. ppm |
| Ethyl iodide: | trace |
| Ethyl acetate: | trace |
| Butyl iodide: | not detected |
| Crotoaldehyde: | not detected |

Flasher 201:
  Interior wall: Ti—Pd alloy
  Temperature: 140° C.
Line 213:
  Composition of gas phase:

| | |
|---|---|
| Acetic acid: | 45.5 wt. % |
| Methanol: | 2.1 wt. % |
| Water: | 4.1 wt. % |
| Methyl iodide: | 20.0 wt. % |
| Methyl acetate: | 28.4 wt. % |

Line 204:
  Methanol feed: 0.2 part by weight per 100 parts by weight of the liquid product feed through the line 213
First Distillation Tower 202:
  Inside wall: Ti

| | |
|---|---|
| Tower top temperature: | 104° C. |
| Tower bottom temperature: | 142° C. |
| Pressure: | 1.8 atm |

Line 232:
  KOH aqueous solution feed:

| | |
|---|---|
| Concentration: | 10 wt. % aqueous solution |
| Feed amount: | 0.02 part by weight per 100 parts by weight of the liquid product feed through the line 213 |

Second Distillation Tower 203:
  Inside wall: Stainless steel SUS316

| | |
|---|---|
| Tower top temperature: | 113° C. |
| Tower bottom temperature: | 134° C. |
| Pressure: | 1.6 atm |

Line 231 (acetic acid product fraction):
  Impurity contents:

| | |
|---|---|
| Water: | below 0.1 wt. % |
| Propionic acid: | 5 wt. ppm |

-continued

| | |
|---|---|
| Iodine: | 6 wt. ppb |
| Permanganate time: | over 240 minutes |

EXAMPLE 9

Example 8 was repeated in the same manner as described except that the hydrogen partial pressure in the reactor was changed as shown in Table 7. The contents of some components in the pressure reduced liquid product through the line 211 were also shown in Table 7. The properties of the acetic acid fraction recovered through the line 231 were shown in Table 8.

TABLE 7

| Experiment No. | 1 | 2 | 3 | 4 |
|---|---|---|---|---|
| Hydrogen partial pressure (kg/cm$^2$) | 2.0 | 4.0 | 8.0 | 2.0 |
| Hydrogen iodide (wt. ppm) | 30 | 32 | 40 | 800 |
| Acetaldehyde (wt. ppm) | 1,020 | 1,730 | 4,360 | 1,310 |
| Propionic acid (wt. ppm) | 60 | 191 | 533 | 75 |
| Ethyl iodide (wt. ppm) | trace | 380 | 1,250 | 120 |
| Butyl iodide (wt. ppm) | ND* | ND* | 2 | 1 |
| Ethyl acetate (wt. ppm) | trace | 340 | 1,330 | 140 |
| Crotoaldehyde (wt. ppm) | ND* | ND* | 2 | ND* |
| Water (wt. %) | 7.0 | 7.1 | 6.7 | 2.0 |
| Carbonylation degree | 0.76 | 0.75 | 0.77 | 0.93 |

ND: not detected

TABLE 8

| Experiment No. | 1 | 2 | 3 | 4 |
|---|---|---|---|---|
| Permanganate time (min.) | >240 | 120 | 60 | 60 |
| Water (wt. %) | <0.1 | <0.1 | <0.1 | <0.1 |
| Propionic acid (wt. ppm) | 21 | 97 | 527 | 33 |
| Iodine (wt. ppb) | 11 | 17 | 200 | 43 |

EXAMPLE 10

Grams (on dry basis) of the Rh-loaded VP resin catalyst obtained in Example 7 was charged in a 200 ml autoclave having an interior surface of titanium together with 100 g of a raw material liquid feed containing 32% by weight of methanol, 17% by weight of methyl iodide, 51% by weight of acetic acid. After pressurizing the autoclave to 1 atm with a hydrogen gas, the mixture in the autoclave was heated to 180° C. with stirring while maintaining the total pressure within the autoclave at 40 kg/cm $^2$G by introduction of CO. The liquid product after 100 minutes reaction had the following composition:

| | |
|---|---|
| Carbonylation degree: | 0.85 |
| Methyl iodide: | 13.4 wt. % |
| Methanol: | 0.9 wt. % |
| Acetic acid: | 67.6 wt. % |
| Methyl acetate: | 14.2 wt. % |
| Water: | 3.9 wt. % |
| Hydrogen iodide: | 25 wt.ppm |
| Acetaldehyde: | 930 wt.ppm |
| Propionic acid: | 10 wt.ppm |

COMPARATIVE EXAMPLE 3

In an autoclave having an interior surface of zirconium was charged a mixed liquid consisting of 29% by weight of methanol, 15% by weight of methyl iodide, 11% by weight of lithium iodide and 45% by weight of acetic acid. Rhodium acetate was mixed into the mixed liquid in an amount so that the resulting mixture had a rhodium content (in terms of elemental Rh) of 450 ppm by weight. After pressurizing the autoclave to 1 atm with a hydrogen gas, the mixture in the autoclave was heated to 180° C. with stirring while maintaining the total pressure within the autoclave at 40 kg/cm$^2$G by introduction of CO. The liquid product after 100 minutes reaction had the following composition:

| | |
|---|---|
| Lithium iodide: | 8.8 wt. % |
| Methyl iodide: | 12.0 wt. % |
| Methanol: | 0.7 wt. % |
| Acetic acid: | 55.4 wt. % |
| Methyl acetate: | 11.6 wt. % |
| Water: | 3.2 wt. % |
| Acetaldehyde: | 1,010 wt.ppm |
| Propionic acid: | 123 wt.ppm |

COMPARATIVE EXAMPLE 4

In an autoclave having an interior surface of zirconium was charged a mixed liquid consisting of 15% by weight of water, 27% by weight of methanol, 15% by weight of methyl iodide, 43% by weight of acetic acid. Rhodium acetate was mixed into the mixed liquid in an amount so that the resulting mixture had a rhodium content (in terms of elemental Rh) of 500 ppm by weight. After pressurizing the autoclave to 1 atm with a hydrogen gas, the mixture in the autoclave was heated to 180° C. with stirring while maintaining the total pressure within the autoclave at 40 kg/cm$^2$G by introduction of CO. The liquid product after 100 minutes reaction had the following composition:

| | |
|---|---|
| Methyl iodide: | 11.0 wt. % |
| Acetic acid: | 72.7 wt. % |
| Methyl acetate: | 1.3 wt. % |
| Water | 14.9 wt. % |
| Acetaldehyde: | 1,320 wt.ppm |
| Propionic acid: | 1,210 wt.ppm |

What is claimed is:

1. A process for the production of a carbonyl compound, comprising the steps of:
    (a) reacting a carbonylatable compound with a carbon monoxide feed in a reactor in the presence of carbonylation catalyst including a noble metal complex supported on a porous, cross-linked vinylpyridine resin to obtain a liquid product containing the carbonyl compound; and
    (b) discharging said liquid product from said reactor and separating said carbonyl compound from said liquid product said discharged liquid product in a flasher and/or a distillation tower,
    wherein step (a) is performed at a temperature of 140–250° C and at a carbon monoxide partial pressure of 7–30 kg/cm$^2$ and a hydrogen partial pressure is maintained at 0.1–5 kg/cm$^2$ while maintaining the water content and the carbonylation degree of the reaction solution within said reactor at 0.5–10% by weight and within the range of 0.5–0.9, respectively, and
    wherein the water content and the carbonylation degree of said discharged liquid product are maintained at not greater than 10% by weight and not greater than 0.9, respectively.

2. A process as claimed in claim 1, wherein said carbonylatable compound is selected from methanol and dimethyl ether and said noble metal is rhodium, and wherein step (a) is performed in the presence of an alkyl iodide, so that acetic acid is produced as said carbonyl compound.

3. A process as claimed in claim 1, wherein said carbon monoxide feed contains 0.5–5% by volume of hydrogen.

4. A process for the production of a carbonyl compound, comprising the steps of:

(a) reacting a carbonylatable compound with a carbon monoxide feed in a reactor in the presence of carbonylation catalyst including a noble metal complex supported on a porous cross-linked vinylpyridine resin to obtain a liquid product containing the carbonyl compound; and (b) discharging said liquid product from said reactor and introducing said discharged liquid product into a first or a series of first to n-th distillation towers successively, where n is at least two, thereby to separate said carbonyl compound from said liquid product, wherein the interior surface of said reactor is formed of titanium or a titanium-palladium alloy, wherein step (a) is performed at a temperature of 140–250° C., a carbon monoxide partial pressure of 7–30 kg/cm$^2$ and a hydrogen partial pressure of 0.1–5 kg/cm$^2$ while maintaining the water content and the carbonylation degree of the reaction solution within said reactor at 0.5–10% by weight and within the range of 0.5–0.9, respectively, wherein the water content and the carbonylation degree of said discharged liquid product are maintained at not greater than 10% by weight and not greater than 0.9, respectively, and wherein the water content of the fraction containing said carbonyl compound obtained in said first distillation tower is adjacent at 3,000 ppm by weight or less.

5. A process for the production of a carbonyl compound, comprising the steps of:

(a) reacting a carbonylatable compound with a carbon monoxide feed in a reactor in the presence of carbonylation catalyst including a noble metal complex supported on a porous, cross-linked vinylpyridine resin to obtain a liquid product containing the carbonyl compound, and (b) discharging said liquid product from said reactor and introducing said discharged liquid product into a first or a series of first to n-th distillation towers successively, where n is at least two, thereby to separate said carbonyl compound from said liquid product, wherein the interior surface of said first distillation tower is formed of titanium or a titanium-palladium alloy, wherein step (a) is performed at a temperature of 140–250° C. a carbon monoxide partial pressure of 7–30 kg/cm$^2$ and a hydrogen partial pressure of 0.1–5 kg/cm$^2$ while maintaining the water content and the carbonylation degree of the reaction solution within said reactor at 0.5–10% by weight and within the range of 0.5–0.9, respectively wherein the water content and the carbonylation degree of said discharged liquid product are maintained at not greater than 10% by weight and not greater than 0.9, respectively, and wherein the water content of the fraction containing said carbonyl compound obtained in said first distillation tower is adjacent at 3,000 ppm by weight or less.

6. A process for the production of a carbonyl compound, comprising the steps of:

(a) reacting a carbonylatable compound with a carbon monoxide feed in a reactor in the presence of carbonylation catalyst including a noble metal complex supported on a porous, cross-linked vinylpyridine resin to obtain a liquid product containing the carbonyl compound; and (b) discharging said liquid product from said reactor and introducing said discharged liquid product into a first or a series of first to n-th distillation towers successively, where n is at least two, thereby to separate said carbonyl compound from said liquid product, wherein said liquid product is introduced into a flasher to separate said liquid product into a gas phase and a liquid phase, wherein said gas phase is fed to said first distillation tower, wherein the interior surface of said flasher and/or distillation tower is formed of titanium or a titanium-palladium alloy, wherein step (a) is performed at a temperature of 140–250° C., a carbon monoxide partial pressure of 7–30 kg/cm$^2$ and a hydrogen partial pressure of 0.1–5 kg/cm$^2$ while maintaining the water content and the carbonylation degree of the reaction solution within said reactor at 0.5–10% by weight and within the range of 0.5–0.9, respectively, wherein the water content and the carbonylation degree of said discharged liquid product are maintained at not greater than 10% by weight and not greater than 0.9, respectively, and wherein the water content of the fraction containing said carbonyl compound obtained in said first distillation tower is adjacent at 3,000 ppm by weight or less.

7. A process for the production of a carbonyl compound, comprising the steps of:

(a) reacting a carbonylatable compound with carbon monoxide in a reactor in the presence of a carbonylation catalyst including a noble metal complex supported on a porous, cross-linked vinylpyridine resin to obtain a liquid product containing the carbonyl compound; and (b) separating said carbonyl compound from said liquid product in a flasher and/or a distillation tower, wherein step (a) is performed while maintaining the water content of said liquid product at not greater than 10% by weight, and wherein the interior surface of said flasher and/or distillation tower is formed of titanium or a titanium-palladium alloy.

8. A process as claimed in claim 7, wherein said carbonylatable compound is selected from methanol and dimethyl ether and said noble metal is rhodium, and wherein step (a) is performed in the presence of an alkyl iodide, so that acetic acid is produced as said carbonyl compound.

9. A process as claimed in claim 7, wherein step (a) is performed while maintaining the carbonylation degree of said liquid product within the range of 0.5–0.9.

10. A process as claimed in claim 7, wherein step (b) is performed with a combination of said flasher and said distillation tower, wherein said distillation tower is equipped with a reboiler and a condenser, and wherein the interior surface of each of said reboiler and said condenser is formed of a titanium-palladium alloy.

11. A process as claimed in claim 7, wherein the interior surface of said reactor is formed of titanium or a titanium-palladium alloy.

12. A process for the production of a carbonyl compound, comprising the steps of:

(a) reacting a carbonylatable compound with carbon monoxide in a reaction zone in the presence of a carbonylation catalyst including a noble metal complex supported on a porous, cross-linked vinylpyridine resin to obtain a liquid product containing the carbonyl compound and a gas product containing unreacted carbon monoxide;

(b) discharging said liquid product from said reaction zone and introducing same into a pressure reducing device to reduce the pressure of said discharged liquid product to obtain a pressure-reduced liquid product;

(c) withdrawing said gas product from said reaction zone;

(d) mixing said pressure-reduced liquid product with said gas product to form a mixture; and (e) separating said carbonyl compound from said mixture in a separation zone.

13. A process as claimed in claim 12, wherein step (d) is performed in said separation zone by separately introducing said pressure-reduced liquid product and said gas product thereinto.

14. A process as claimed in claim 13, wherein said gas product is heated before being introduced into said separation zone.

15. A process as claimed in claim 13, wherein said separation zone is a distillation tower and wherein said gas product is fed to a bottom of said distillation tower.

16. A process as claimed in claim 13, wherein said separation zone comprises a gas-liquid separator and a distillation tower, and wherein said pressure-reduced liquid product and said gas product is fed to said gas-liquid separating zone to separate said mixture into a gas phase containing said carbonyl compound and a liquid phase, said gas phase being withdrawn from said gas-liquid separator and introduced into said distillation tower to recover said carbonyl compound.

17. A process as claimed in claim 12, wherein steps (d) and (e) comprise mixing said pressure-reduced liquid product with said gas product to form a mixture, feeding said mixture to said separation zone, and separating said carbonyl compound from said mixture in said separation zone.

18. A process as claimed in claim 17, wherein said mixture is heated before introduction into said separation zone.

19. A process as claimed in claim 17, wherein said separation zone is a distillation tower and wherein said gas product is fed to a bottom of said distillation tower.

20. A process as claimed in claim 17, wherein said separation zone comprises a gas-liquid separator and a distillation tower, and wherein said mixture is fed to said gas-liquid separating zone to separate said mixture into a gas phase containing said carbonyl compound and a liquid phase, said gas phase being withdrawn from said gas-liquid separator and introduced into said distillation tower to recover said carbonyl compound.

21. A process as claimed in claim 12, wherein said carbonylatable compound is selected from methanol and dimethyl ether and said noble metal is rhodium, wherein step (a) is performed in the presence of an alkyl iodide, so that acetic acid is produced as said carbonyl compound, and wherein said withdrawn gas product is scrubbed with methanol before mixing with said pressure-reduced liquid product.

22. A process for the production of a carbonyl compound, comprising the steps of:

(a) reacting a carbonylatable compound with carbon monoxide in the presence of a carbonylation catalyst including a noble metal complex supported on a porous, cross-linked vinylpyridine resin to obtain a liquid product containing the carbonyl compound; and (b) separating said carbonyl compound from said liquid product, step (a) being performed while maintaining the concentration of pyridine compounds in said liquid product within the range of 0.5–200 ppm by weight in terms of elemental nitrogen.

23. A process as claimed in claim 22, wherein said carbonylatable compound is selected from methanol and dimethyl ether and said noble metal is rhodium, and wherein step (a) is performed in the presence of an alkyl iodide, so that acetic acid is produced as said carbonyl compound.

24. A process as claimed in claim 22, wherein said carbonylatable compound is methyl acetate and said noble metal is rhodium, and wherein step (a) is performed in the presence of an alkyl iodide, so that acetic anhydride is produced as said carbonyl compound.

* * * * *